United States Patent
Gregory et al.

(10) Patent No.: US 9,574,211 B2
(45) Date of Patent: Feb. 21, 2017

(54) METHODS AND COMPOSITIONS FOR PREVENTION OR TREATMENT OF A DISEASE

(71) Applicant: Sangamo BioSciences, Inc., Richmond, CA (US)

(72) Inventors: Philip D. Gregory, Richmond, CA (US); Michael C. Holmes, Richmond, CA (US)

(73) Assignee: Sangamo BioSciences, Inc., Richmond, CA (US)

( * ) Notice: Subject to any disclaimer, the term of this patent is extended or adjusted under 35 U.S.C. 154(b) by 0 days.

(21) Appl. No.: 14/711,078

(22) Filed: May 13, 2015

(65) Prior Publication Data

US 2015/0329875 A1 Nov. 19, 2015

Related U.S. Application Data

(60) Provisional application No. 61/992,676, filed on May 13, 2014.

(51) Int. Cl.
| | |
|---|---|
| *C07H 21/04* | (2006.01) |
| *C12N 15/90* | (2006.01) |
| *C12N 9/22* | (2006.01) |
| *A61K 39/00* | (2006.01) |
| *C07K 14/00* | (2006.01) |

(52) U.S. Cl.
CPC .............. *C12N 15/90* (2013.01); *A61K 39/00* (2013.01); *C07K 14/00* (2013.01); *C12N 9/22* (2013.01); *C07K 2319/50* (2013.01); *C07K 2319/71* (2013.01); *C07K 2319/81* (2013.01)

(58) Field of Classification Search
CPC .................................................. C07H 21/04
See application file for complete search history.

(56) References Cited

U.S. PATENT DOCUMENTS

| | | | |
|---|---|---|---|
| 5,356,802 | A | 10/1994 | Chandrasegaran |
| 5,436,150 | A | 7/1995 | Chandrasegaran |
| 5,487,994 | A | 1/1996 | Chandrasegaran |
| 5,789,538 | A | 8/1998 | Rebar et al. |
| 5,925,523 | A | 7/1999 | Dove et al. |
| 6,007,988 | A | 12/1999 | Choo |
| 6,013,453 | A | 1/2000 | Choo |
| 6,140,081 | A | 10/2000 | Barbas |
| 6,140,466 | A | 10/2000 | Barbas, III et al. |
| 6,200,759 | B1 | 3/2001 | Dove et al. |
| 6,242,568 | B1 | 6/2001 | Barbas, III et al. |
| 6,410,248 | B1 | 6/2002 | Greisman et al. |
| 6,453,242 | B1 | 9/2002 | Eisenberg et al. |
| 6,479,626 | B1 | 11/2002 | Kim et al. |
| 6,503,717 | B2 | 1/2003 | Case et al. |
| 6,534,261 | B1 | 3/2003 | Cox, III et al. |
| 6,599,692 | B1 | 7/2003 | Case et al. |
| 6,607,882 | B1 | 8/2003 | Cox, III et al. |
| 6,689,558 | B2 | 2/2004 | Case |
| 6,723,551 | B2 | 4/2004 | Kotin |
| 6,733,970 | B2 | 5/2004 | Choo et al. |
| 6,746,838 | B1 | 6/2004 | Choo et al. |
| 6,794,136 | B1 | 9/2004 | Eisenberg et al. |
| 6,824,978 | B1 | 11/2004 | Cox, III et al. |
| 6,866,997 | B1 | 3/2005 | Choo et al. |
| 6,903,185 | B2 | 6/2005 | Kim et al. |
| 6,933,113 | B2 | 8/2005 | Case et al. |
| 6,979,539 | B2 | 12/2005 | Cox, III et al. |
| 7,013,219 | B2 | 3/2006 | Case et al. |
| 7,030,215 | B2 | 4/2006 | Liu et al. |
| 7,067,317 | B2 | 6/2006 | Rebar et al. |
| 7,070,934 | B2 | 7/2006 | Cox, III et al. |
| 7,074,596 | B2 | 7/2006 | Darzynkiewicz et al. |
| 7,153,949 | B2 | 12/2006 | Kim et al. |
| 7,163,824 | B2 | 1/2007 | Cox, III et al. |
| 7,241,573 | B2 | 7/2007 | Choo et al. |
| 7,241,574 | B2 | 7/2007 | Choo et al. |
| 7,253,273 | B2 | 8/2007 | Collingwood |
| 7,262,054 | B2 | 8/2007 | Jamieson et al. |
| 7,297,491 | B2 | 11/2007 | Joung et al. |
| 7,361,635 | B2 | 4/2008 | Miller et al. |
| 7,888,121 | B2 | 2/2011 | Urnov et al. |
| 7,914,796 | B2 | 3/2011 | Miller et al. |
| 7,951,925 | B2 | 5/2011 | Ando et al. |
| 7,972,854 | B2 | 7/2011 | Miller et al. |
| 8,034,598 | B2 | 10/2011 | Miller |
| 8,110,379 | B2 | 2/2012 | DeKelver et al. |
| 8,153,773 | B2 | 4/2012 | Jemielity et al. |
| 8,409,861 | B2 | 4/2013 | Guschin et al. |
| 8,420,782 | B2 | 4/2013 | Bonas et al. |
| 8,440,431 | B2 | 5/2013 | Voytas et al. |
| 8,563,314 | B2 | 10/2013 | Gregory et al. |
| 8,586,526 | B2 | 11/2013 | Gregory et al. |

(Continued)

FOREIGN PATENT DOCUMENTS

| | | |
|---|---|---|
| GB | 2338237 A | 12/1999 |
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |

(Continued)

OTHER PUBLICATIONS

Sander et al. (Nat Biotechnol. Aug. 5, 2011; 29(8): 697-698).*
Desvignes et al. (Gene 2014, 546:386-389).*
Hu et al. (PloS One 8(5): e63074 May 2013).*
Gaj et al. (Trends in Biotechnology Jul. 2013, vol. 31: 397-404).*
Aagaard, et al., "RNAI Therapeutics: Principles, Prospects and Challenges," *Adv. Drug Deliv. Rev.* 59(2-3): 75-86 (2007).

(Continued)

*Primary Examiner* — Kimberly Chong
(74) *Attorney, Agent, or Firm* — Pasternak Patent Law; Susan Abrahamson

(57) ABSTRACT

Methods and compositions for treatment of a genetic disease are provided.

12 Claims, 4 Drawing Sheets

(56) References Cited

U.S. PATENT DOCUMENTS

| | | | |
|---|---|---|---|
| 8,623,618 | B2 | 1/2014 | Doyon et al. |
| 8,697,359 | B1 | 4/2014 | Zhang |
| 8,932,814 | B2 | 1/2015 | Cong et al. |
| 2003/0232410 | A1 | 12/2003 | Liljedahl et al. |
| 2005/0026157 | A1 | 2/2005 | Baltimore et al. |
| 2005/0208489 | A1 | 9/2005 | Carroll et al. |
| 2006/0063231 | A1 | 3/2006 | Li et al. |
| 2006/0105360 | A1 | 5/2006 | Croce et al. |
| 2007/0134796 | A1 | 6/2007 | Holmes et al. |
| 2008/0131962 | A1 | 6/2008 | Miller |
| 2008/0159996 | A1 | 7/2008 | Ando et al. |
| 2009/0117617 | A1 | 5/2009 | Holmes et al. |
| 2010/0047805 | A1 | 2/2010 | Wang |
| 2010/0218264 | A1 | 8/2010 | Cui et al. |
| 2010/0235936 | A1* | 9/2010 | McCaffrey ......... C12N 15/1131 800/18 |
| 2010/0291048 | A1 | 11/2010 | Holmes et al. |
| 2011/0201055 | A1 | 8/2011 | Doyon et al. |
| 2011/0207221 | A1 | 8/2011 | Cost et al. |
| 2011/0265198 | A1 | 10/2011 | Gregory et al. |
| 2011/0281361 | A1 | 11/2011 | DeKelver et al. |
| 2011/0301073 | A1 | 12/2011 | Gregory et al. |
| 2012/0017290 | A1 | 1/2012 | Cui et al. |
| 2012/0192298 | A1 | 7/2012 | Weinstein et al. |
| 2012/0195936 | A1 | 8/2012 | Rudolph et al. |
| 2013/0122591 | A1 | 5/2013 | Cost et al. |
| 2013/0137104 | A1 | 5/2013 | Cost et al. |
| 2013/0177960 | A1 | 7/2013 | Rebar |
| 2013/0177983 | A1 | 7/2013 | Rebar |
| 2013/0253040 | A1 | 9/2013 | Miller et al. |
| 2013/0326645 | A1 | 12/2013 | Cost et al. |
| 2014/0687971 | | 3/2014 | Doudna et al. |
| 2015/0056705 | A1 | 2/2015 | Conway et al. |

FOREIGN PATENT DOCUMENTS

| | | |
|---|---|---|
| WO | WO 01/60970 A2 | 8/2001 |
| WO | WO 01/88197 A2 | 11/2001 |
| WO | WO 02/16536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO 2010/079430 A1 | 7/2010 |

OTHER PUBLICATIONS

Abifadel, et al., "Mutations in PCSK9 Cause Autosomal Dominant Hypercholesterolemia," *Nature Genetics* 34(2):154-156 (2003).

Ajioka, et al., "Biosynthesis of Heme in Mammals," *Biochimica et Biophysica Acta* 1763:723-736 (2006).

Al-Saikan, et al., "The Gene Therapy Revolution in Ophthalmology," *Saudi Journal of Ophthalmology* 27:107-111 (2013).

Barnard, et al., "Gene Therapy for Choroideremia Using an Adeno-Associated Viral (AAV) Vector," *Cold Spring Harbor Laboratory Press* 5:a017293 (2015).

Beerli, et al., "Engineering Polydactyl Zinc-Finger Transcription Factors," *Nature Biotechnol.* 20:135-141(2002).

Beurdeley, et al., "Compact Designer Talens for Efficient Genome Engineering," *Nature Communications* 4:1762 (2013) doi:10.10.38/ncomms2782.

Bobik, "Apolipoprotein CIII and Atherosclerosis: Beyond Effects on Lipid Metabolism," *Circulation* 118:702-704 (2008).

Boch, et al., "Breaking the Code of DNA Binding Specificity of Tal-Type III Effectors," *Science* 326:1509-1512 (2009).

Boissel, et al., "Megatals: A Rare-Cleaving Nuclease Architecture for Therapeutic Genome Engineering," *Nucl. Acid Res.* 1-13 (2013) doi: 10.1093/nar/gkt1224.

Bonas, et al., "Genetic and Structural Characterization of the Avirulence Gene AVRBS3 From Xanthomonas Campestris PV. Vesicatoria," *Mol. Gen. Genet.* 218:127-136 (1989).

Bourdillon, et al., "ICAM-1 Deficiency Reduces Atherosclerotic Lesions in Double-Knockout Mice (APOE-/-ICAM-1-/-) Fed a Fat or a Chow Diet," *Arterioscler. Thromb. Vasc. Biol.* 20:2630-2635 (2000).

Brodsky, "Advances in the Diagnosis and Therapy of Paroxysmal Nocturnal Hemoglobinuria," *Blood Rev.* 22(2):65-74 (2008).

Byrne, et al., "Retinoschisin Gene Therapy in Photoreceptors, Müller Glia, or All Retinal Cells in the RS1H-/-Mouse," *Gene Ther.* 21(6):585-592 (2014) doi:10.1038/gt.2014.31.

Caillet-Boudin, et al., "Brain Pathology in Myotonic Dystrophy: When Tauopathy Meets Spliceopathy and Rnaopathy," *Frontiers in Molecular Neuroscience* 6(570):1-20 (2014).

Chasman, et al., "Polymorphism in the Apolipoprotein(A) Gene, Plasma Lipoprotein (A), Cardiovascular Disease, and Low-Dose Aspirin Therapy," *Atherosclerosis* 203(2):371-376 (2009) doi:10.1016/j.atherosclerosis.2008.07.019.

Chacon-Camacho, et al., "Review and Update on the Molecular Basis of Leber Congenital Amaurosis," *World J. Clin. Cases* 3(2):112-124 (2015) ISSN 2307-8960 (online).

Chan, et al., "Hypercoagulable States in Cardiovascular Disease," *Circulation* 118:2286-2297 (2008).

Cheng, et al., "Differential Microrna Expression in Renal Cell Carcinoma," *Oncol. Let.* 6:769-776 (2013).

Choi, et al., "Metabolism and Bioenergenetics: Suppression of Diacylglycerol Acyltransferase-2 (DGAT2), But Not DGAT1, With Antisense Oligonucleotides Reverses Diet-Induced Hepatic Steatosis and Insulin Resistance," *The Journal of Biological Chemistry* 282(31):22678-22688 (2007).

Choo, et al., "Advances in Zinc Finger Engineering," *Curr. Opin. Struct. Biol.* 10:411-416 (2000).

Cohen, et al., "Sequence Variations in PCSK9, Low LDL, and Protection Against Coronary Heart Disease," *The New England Journal of Medicine* 354(12):1264-1272 (2006).

Cong, et al., "Multiplex Genome Engineering Using CRISPR/CAS Systems," Sciencexpress/10.1126.science.1231143 (2013).

Davidson, et al., "Current Prospects for RNA Interference-Based Therapies," *Genetics* 12:329 (2011).

de Jorge, et al., "The Development of Atypical Hemolytic Uremic Syndrome Depends on Complement C5," *J. Am. Soc. Nephrol.* 22:137-145 (2011).

Di Bisceglie, "Hepatitis B and Hepatocellular Carcinoma," *Hepatology* 49(5 Suppl):S56-S60 (2009) doi:10.1002/hep.22962.

Durai, et al.., "Zinc Finger Nucleases: Custom-Designed Molecular Scissors for Genome Engineering of Plant and Mammalian Cells," *Nucleic Acids Research* 33(18):5978-5990 (2005).

Esquela-Kerscher and Slack, "Oncomirs—Micrornas With a Role in Cancer," *Nat. Rev.* 6:259-269 (2006).

Esvelt, et al., "Orthogonal CAS9 Proteins for RNA-Guided Gene Regulation and Editing," *Nat. Meth.* 10(11):1116 (2013).

Fernandez-Ruiz, et al., "Protein Tyrosine Phosphatase-1B Modulates Pancreatic B-Cell Mass," *PLOS One* 9(2):e90344 (2014).

Fischer, "Cap in Hand" *Cell Cycle* 8:16, 2535-2541 (2009).

Fonfara, et al., "Phylogeny of CAS9 Determines Functional Exchangeability of Dual-Rna and CAS9 Among Orthologous Type II CRISPR-CAS Systems," *Nuc. Acid. Res.* 42(4):2377-2590 (2013).

Fried, et al., "Peginterferon ALFA-2a Plus Ribavirin for Chronic Hepatitis C Virus Infection," *N. Engl. J. Med.* 347(13):975-982 (2002).

Fu, et al., "Improving CRISPR-CAS Nuclease Specificity Using Truncated Guide RNAS," *Nature Biotech.* 32(3):279-284 (2014)

Fujita, et al., "RNAI Therapeutic Platforms for Lung Diseases," *Pharmaceuticals* 6:223-250 (2013) doi:10.3390/ph6020223.

Furling, et al., "Viral Vector Producing Antisense RNA Restores Myotonic Dystrophy Myoblast Functions," *Gene Therapy* 10:795-802 (2003).

Ganz, "Hepcidin and Iron Regulation, 10 Years Later," *Blood* 117:4425-4433 (2011).

Gerbert et al., "Miravirsen (SPC3649) Can Inhibit the Biogenesis of MIR-122," *Nuc. Acid. Res.* 42(1):609-621 (2014).

Grover, et al., "Re-Programming DNA-Binding Specificity in Zinc Finger Proteins for Targeting Unique Address in a Genome," *Syst. Synth. Biol.* 4:323-329 (2010).

(56) References Cited

OTHER PUBLICATIONS

Gruppo, et al., "Eculizumab for Congenital Atypical Hemolytic—Uremic Syndrome," *New England J. Med.* 360:5 (2009).
Guschin, et al., "A Rapid and General Assay for Monitoring Endogenous Gene Modification," *Methods Mol. Biol.* 649:247-256 (2010).
Haft, et al., "A Guild of 45 CRISPR-Associated (CAS) Protein Families and Multiple CRISPR/CAS Subtypes Exist in Prokaryotic Genomes," *PLoS Comput. Biol.* 1(6):474-483 (2005).
Halegoua-De Marzio, et al., "Then and Now: The Progress in Hepatitis B Treatment Over the Past 20 Years," *World J. Gastroenterol.* 20(2):401-413 (2014).
Haussecker and Kay, "MIR-122 Continues to Blaze the Trail for Microrna Therapeutics," *Mol. Ther.* 18(2):240-242 (2010).
He, et al., "A Microrna Component of the P53 Tumour Suppressor Network," 447:1130-1135 (2007) doi:10.1038/nature05939.
Henshall, et al., "Micrornas in the Pathophysiology and Treatment of Status Epilepticus," *Front Mol. Neurosci.* 6(37):1-11 (2013).
Hermeking, et al., "The MIR-34 Family in Cancer and Apoptosis," *Cell Death and Differentiation* 17:193-199 (2010).
Heuer, et al., "Repeat Domain Diversity of AVRBS3-Like Genes in Ralstonia Solanacearum Strains and Association With Host Preferences in the Field," *Appl. and Envir. Micro.* 73(13):4379-4384 (2007).
Hillmen, et al., "Long-Term Safety and Efficacy of Sustained Eculizumab Treatment in Patients With Paroxysmal Nocturnal Haemoglobinuria," *British Journal of Haematology* 162:62-73 (2013).
Hnik, et al., "Antisense Oligonucleotide Therapy in Diabetic Retinopathy," *Journal of Diabetes Science and Technology* 3(4):924-930 (2009).
Hsu, et al., "DNA Targeting Specificity of RNA-Guided CAS9 Nucleases," *Nature Biotech.* 31(9):827-832 (2013) doi:10.1338/nbt.2647.
Hwang, et al., "Efficient In Vivo Genome Editing Using RNA-Guided Nucleases," *Nature Biotechnology* 31(3):227 (2013).
Innerarity, et al., "Familial Defective Apolipoprotein B-100: Low Density Lipoproteins With Abnormal Receptor Binding," *PNAS USA* 84:6919-6923 (1987).
Isalan, et al., "A Rapid, Generally Applicable Method to Engineer Zinc Fingers Illustrated by Targeting the HIV-1 Promoter," *Nat. Biotechnol.* 19:656-660 (2001).
Jansen, et al., "Identification of Genes That Are Associated With DNA Repeats in Prokaryotes," *Molecular Microbiology* 43(6):1565-1575 (2002).
Janssen, et al., "Treatment of HCV Infection by Targeting Microrna," *New Eng. J. Med.* 368(18):1685-1694(2013).
Jarnicki, et al., "STAT3: Linking Inflammation to Epithelial Cancer—More Than a "Gut" Feeling?," *Cell Division* 5(14):1-15 (2010).
Jia, et al., "Cap-Dependent Translation Initiation Factor EIF4E: An Emerging Anticancer Drug Target," *Medicinal Research Reviews* 1-29 (2012).
Jiang, et al., "The Effects of Hepatitis B Virus Integration Into the Genomes of Hepatocellular Carcinoma Patients," *Genome Res.* 22: 93-601 (2012).
Jinek, et al., "A Programmable Dual-RNA-Guided DNA Endonuclease in Adaptive Bacterial Immunity," *Science* 337:816 (2012).
Johanssen, et al., "Mifepristone (RU 486) in Cushing's Syndrome," *European Journal of Endocrinology* 157:561-569 (2007).
Johnson, et al., "The Transthyretin Amyloidoses: From Delineating the Molecular Mechanism of Aggregation Linked to Pathology to a Regulatory Agency Approved Drug," *J. Mol. Biol.* 421(2-3):185-203 (2012) doi:10.1016/j.jmb.2011.12.060.
Jun and Lou, "Taking Aim At the Extracellular Matrix: CCN Proteins As Emerging Therapeutic Targets," *Nat. Rev. Drug Discov.* 10(12):945-963 (2013) doi:10.1038/nrd3599.

Kay, et al., "A Bacterial Effector Acts As a Plant Transcription Factor and Induces a Cell Size Regulator," *Science* 318:648-651 (2007).
Kim, et al., "Insertion and Deletion Mutants of Fok I Restriction Endonuclease," *J. Biol. Chem.* 269:31,978-31,982 (1994).
Kim, et al., "Chimeric Restriction Endonuclease," *PNAS USA* 91:883-887 (1994).
Kim, et al., "Hybrid Restriction Enzymes: Zinc Finger Fusions to Fok I Cleavage Domain," *PNAS USA* 93(3):1156-1160 (1996).
Kormann, et al., "Expression of Therapeutic Proteins After Delivery of Chemically Modified MRNA in Mice," *Nature Biotechnology* 29(2):154-157 (2011).
Kur, et al., "Cellular and Physiological Mechanisms Underlying Blood Flow Regulation in the Retina Choroid in Health Disease," *Prog. Retin. Eye Res.* 31(5):377-406 (2012) doi:10.1016/j.preteyeres.2012.04.004.
Kyutoku, et al., "Inhibition of Neointima Formation Through DNA Vaccination for Apolipoprotein(A): A New Therapeutic Strategy for Lipoprotein(A)," *Scientific Reports* 3(1600):1-9 (2013).
Lagerros, et al., "Obesity Management: What Brings Success?," *Therapeutic Advances in Gastroenterology* 6(1):77-88 (2013).
Leask, "Possible Strategies for Anti-Fibrotic Drug Intervention in Scleroderma," *J. Cell Commun. Signal.* 5:125-129 (2011).
Lewis, "Expanding the Clinical Indications for A1-Antitrypsin Therapy," *Molecular Medicine* 18:957-970 (2012).
Li, et al., "Inhibition of Growth and Metastasis of Human Hepatocellular Carcinoma by Antisense Oligonucleotide Targeting Signal Transducer and Activator of Transcription 3," *Clin. Cancer Res.* 12:7140-7148 (2006).
Li, et al., "In Vivo Genome Editing Restores Haemostasis in a Mouse Model of Haemophilia," *Nature* 475(7355):217-221 (2011).
Li, et al., "Functional Domains in Fok I Restriction Endonuclease," *PNAS USA* 89:4275-4279 (1992).
Li, et al., "Alteration of the Cleavage Distance of Fok I Restriction Endonuclease by Insertion Mutagenesis," *PNAS USA* 90:2764-2768 (1993).
Liang, et al., "Reduction in Glucagon Receptor Expression by an Antisense Oligonucleotide Ameliorates Diabetic Syndrome in DB/DB Mice," *Diabetes* 53:410-417 (2004).
Liu, et al., "Iron Regulator Hepcidin Exhibits Antiviral Activity Against Hepatitis C Virus," *PLOS One* 7(10):1-8 (2012).
Luo, et al., "ATOH1 Expression Levels Define the Fate of Rat Cochlear Nonsensory Epithelial Cells In Vitro," *Molecular Medicine Reports* 10:15-20 (2014).
Luo, et al., "Photoreceptor Avascular Privilege Is Shielded by Soluble VEGF Receptor-1," *eLife* 2:e00324 (2013).
Maeda, et al., "Targeted Disruption of the Apolipoprotein (2-111 Gene in Mice Results in Hypotriglyceridemia and Protection From Postprandial Hypertriglyceridemia," *The Journal of Biological Chemistry* 269(38):23610-23616 (1994).
Mahmoud, et al., "Differential Effects of Genistein on Prostate Cancer Cells Depend on Mutational Status of the Androgen Receptor," *PLOS One* 8(10):e78479 (2013).
Makarova, et al., "A DNA Repair System Specific for Thermophilic Archaea and Bacteria Predicted by Genomic Context Analysis," *Nucleic Acids Res.* 30:482-496 (2002).
Makarova, et al., "A Putative RNA-Interference-Based Immune System in Prokaryotes: Computational Analysis of the Predicted Enzymatic Machinery, Functional Analogies With Eukaryotic RNAI, and Hypothetical Mechanisms of Action," *Biol. Direct* 1:7 (2006).
Mamane, et al., "EIF4E—From Translation to Transformation," *Oncogene* 23:3172-3179 (2004).
Mazaris, et al., "Molecular Pathways in Prostate Cancer," *Nephro. Urol. Mon.* 5(3):793-800(2013).
Melmed, "Acromegaly Pathogenesis and Treatment," *J. Clin. Invest.* 119:3189-3202 (2009) doi:10.1172/JCI39375.
Moscou, et al., "A Simple Cipher Governs DNA Recognition by TAL Effectors," *Science* 326:1501 (2009).
Mueller and Flotte, "Gene-Based Therapy for Alpha-1 Antitrypsin Deficiency," *COPD*, 10(S1):44-49 (2013).

(56) References Cited

OTHER PUBLICATIONS

Munsunuru, et al., "Exome Sequencing, ANGPTL3 Mutations, and Familial Combined Hypolipidemia," *The New England Journal of Medicine* 363(23):2220-2227 (2010).
Oros, et al., "The Genetic Basis of Familial Hypercholesterolemia: Inheritance, Linkage, and Mutations," *The Application of Clinical Genetics* 3:53-64 (2010).
Okada, et al., "Intercellular Adhesion Molecule-1—Deficient Mice Are Resistant Against Renal Injury After Induction of Diabetes," *Diabetes* 2:2586-2593 (2003).
Pabo, et al., "Design and Selection of Novel CYS2HIS2 Zinc Finger Proteins," *Ann. Rev. Biochem.* 70:313-340 (2001).
Patel and Noureddine, "Micrornas and Fibrosis," *Curr. Opin. Nephrol. Hypertens* 21(4):410-416 (2012) doi: 10.1097/MNH. 0b013e328354e559.
Pepsys, et al., "Targeting C-Reactive Protein for the Treatment of Cardiovascular Disease," *Nature* 440(27):1217-1221 (2006) doi:10. 1038/nature04672.
Perez, et al., "Establishment of HIV-1 Resistance in CD4+ T Cells by Genome Editing Using Zinc-Finger Nucleases," *Nat. Biotechnol.* 26:808-816 (2008).
Ragnarsson, et al., "Cushing's Syndrome: A Structured Short- and Long-Term Management Plan for Patients in Remission," *European Journal of Endocrinology* 169:R139-R152 (2013).
Rijavec, et al., "Hereditary Angioedema Nationwide Study in Slovenia Reveals Four Novel Mutations in SERPING1 Gene," *PLOS One* 8(2):e56712 (2013).
Roberts and Katznelson, "Acromegaly-An Update on Clinical Approach and Management," *US Endocrine Disease* 71-73 (2006).
Salomon, et al., "Reduced Incidence of Ischemic Stroke in Patients With Severe Factor XI Deficiency," *Blood* 111:4113-4117 (2008).
Sander and Joung, "CRISPR-CAS Systems for Genome Editing, Regulation and Targeting," *Nat. Biotechnol.* 32(4):347-355 (2014) doi:10.1038/nbt.2842.
Sarli, et al., "Targeting the Kinesin Spindle Protein: Basic Principles and Clinical Implications," *Clin. Cancer Res.* 14:7583-7587 (2008).
Schuelert, et al., "Involvement of NAV 1.8 Sodium Ion Channels in the Transduction of Mechanical Pain in a Rodent Model of Osteoarthritis," *Arthritis Research & Therapy* 14(R5):1-9.
Schmidt, et al., An RNAi Therapeutic Targeting TMPRSS6 Decreases Iron Overload in Fife Mice and Ameliorates Anemia and Iron Overload in Murine-Thalassemia Intermedia, *Blood* 121:1200-1208 (2013).
Schornack, et al., "Gene-For-Gene-Mediated Recognition of Nuclear-Targeted AVRBS3-Like Bacterial Effector Proteins," *J. Plant Physiol.* 163(3):256-272 (2006).
Schwenger, et al., "Clinical Approaches to Non-Alcoholic Fatty Liver Disease," *World J. Gastroenterol* 20(7):1712-1723 (2014).
Segal, et al., "Custom DNA-Binding Proteins Come of Age: Polydactyl Zinc-Finger Proteins," *Curr. Opin. Biotechnol.* 12:632-637 (2001).
Sheridan, "Phase 3 Data for PCSK9 Inhibitor Wows," *Nature Biotechnology* 31(12):1057-1058 (2013).
Shibuya, "VEGF-VEGFR Signals in Health and Disease," *Biomol. Ther.* 22(1):1-9 (2014).
Solis, et al., "Identification and Expression of Mutations in the Hydroxymethylbilane Synthase Gene Causing Acute Intermittent Porphyria (AIP)," *Molecular Medicine* 5:664-671 (1999).
Straume, et al., "Suppression of Heat Shock Protein 27 Induces Long-Term Dormancy in Human Breast Cancer," *PNAS USA* 1-6 (2012).
Sternberg, et al., "DNA Interrogation by the CRISPR RNA-Guided Endonuclease CAS9," *Nature* 507(7490):62-67 (2014) doi:10.1038/nature13011.
Swarbrick, et al., "Inhibition of Protein Tyrosine Phosphatase-1B With Antisense Oligonucleotides Improves Insulin Sensitivity and Increases Adiponectin Concentrations in Monkeys," *Endocrinology* 150(4):1670-1679 (2009).
Taylor, "G-Quadruplex Poses Quadruple Threat," *Nature* 507:175-177 (2014).
Tebas, et al., "Gene Editing of CCR5 in Autologous CD4 T Cells of Persons Infected With HIV," *New Engl. J. Med.* 370(10):901 (2014).
Tuder, et al., "Lung Disease Associated With A1-Antitrypsin Deficiency," *Proc. Am. Thorac. Soc.* 7:381-386 (2010).
Tse, et al., "Recognizing and managing hereditary angioedema," Abstract *Cleveland Clinic Journal of Medicine* 80(5):297-308 (2013).
Umov, et al., "Highly Efficient Endogenous Human Gene Correction Using Designed Zinc-Finger Nucleases," *Nature* 435(7042):646-651 (2005).
Vidyasagar, et al., "Heat Shock Protein 27 (HSP27): Biomarker of Disease and Therapeutic Target," *Fibrogenesis & Tissue Repair* 5:7 (2012).
Watts, et al., "Reduction of Hepatic and Adipose Tissue Glucocorticoid Receptor Expression With Antisense Oligonucleotides Improves Hyperglycemia and Hyperlipidemia in Diabetic Rodents Without Causing Systemic Glucocorticoid Antagonism," *Diabetes* 54:1846-1853 (2005).
Wolf, et al., "Pharmacodynamic Consequences of Administration of VLA-4 Antagonist CDP323 to Multiple Sclerosis Subjects: A Randomized, Double-Blind Phase 1/2 Study," *PLOs One* 8(3):e58438 (2013).
Wu, et al., "Genome-Wide Binding of the CRISPR Endonuclease CAS9 in Mammalian Cells," *Nature Biotech.* 32:670-676 (2014) doi: 10.1038/nbt2889.
Yang, et al., "Elevated Factor XI Activity Levels Are Associated With an Increased Odds Ratio for Cerebrovascular Events," *Am J. Clin. Pathol.* 126:411-415 (2006).
Yang, et al., "Purification, Cloning, and Characterization of the Cel I Nuclease," *Biochemistry* 39:3533-3541 (2000).
Yang, et al., "Serum Micrornas: A New Diagnostic Method for Colorectal Cancer," *Biomed. Rep.* 1(4):495-498 (2013).
Yasuda, et al., "AAV8-Mediated Gene Therapy Prevents Induced Biochemical Attacks of Acute Intermittent Porphyria and Improves Neuromotor Function," *Molecular Therapy* 18(1):17-22 (2010).
Yu, et al., "An Engineered VEGF-Activating Zinc Finger Protein Transcription Factor Improves Blood Flow and Limb Salvage in Advanced-Age Mice," *FASEB J.* 20:479-481 (2006).
Yu, et al., "Peripheral Reduction of FGFR4 With Antisense Oligonucleotides Increases Metabolic Rate and Lowers Adiposity in Diet-Induced Obese Mice," *PLOs* 8(7):e66923 (2013).
Yusa, et al., "Targeted Gene Correction of A1-Antitrypsin Deficiency in Induced Pluripotent Stem Cells," *Nature* 478:391-396 (2011).
Zanetta, et al., "Molecular, Genetic and Stem Cell-Mediated Therapeutic Strategies for Spinal Muscular Atrophy (SMA)," *J. Cell. Mol. Med.* 18(2):187-196 (2014).
Zhu, et al., "Microrna Expression Abnormalities in Limited Cutaneous Scleroderma and Diffuse Cutaneous Scleroderma," *J. Clin. Immunol.* 32(3):514-522 (2012) doi: 10.1007/s10875-011-9647-y.
Zuber, et al., "RNAI Screen Identifies BRD4 As a Therapeutic Target in Acute Myeloid Leukaemia," *Nature* 478(7370):524-528 (2012) doi:10.1038/nature10334.

* cited by examiner

☐ = Exon
■ = miR encoding sequence
▨ = p53 binding site

34c

34a

METHODS AND COMPOSITIONS FOR PREVENTION OR TREATMENT OF A DISEASE

CROSS-REFERENCE TO RELATED APPLICATIONS

The present application claims the benefit of U.S. Provisional Application No. 61/992,676, filed May 13, 2014, the disclosure of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jun. 11, 2015, is named 83250119SL.txt and is 6,380 bytes in size.

TECHNICAL FIELD

The present disclosure is in the field of genome engineering of cells, especially for the treatment or prevention of a human disease.

BACKGROUND

Gene therapy and modulation of gene expression holds enormous potential for a new era in human medicine. These methodologies will allow treatment for conditions that heretofore have not been addressable by standard medical practice.

Recombinant transcription factors comprising the DNA binding domains from zinc finger proteins ("ZFPs") or TAL-effector domains ("TALEs") have the ability to regulate gene expression of endogenous genes (see, e.g., U.S. Pat. Nos. 8,586,526; 6,534,261; 6,599,692; 6,503,717; 6,689,558; 7,067,317; 7,262,054). Clinical trials using these engineered transcription factors containing zinc finger proteins have shown that these novel transcription factors are capable of treating various conditions. (see, e.g., Yu et al. (2006) *FASEB J.* 20:479-481).

Another area of gene therapy that is especially promising is the ability to genetically engineer a cell to cause that cell to express a product not previously being produced in that cell. Examples of uses of this technology include the insertion of a gene encoding a novel therapeutic protein, insertion of a coding sequence encoding a protein that is lacking in the cell or in the individual, insertion of a wild type gene in a cell containing a mutated gene sequence, and insertion of a sequence that encodes a structural nucleic acid such as a microRNA or siRNA.

Transgenes can be delivered to a cell by a variety of ways such that the transgene becomes integrated into the cell's own genome and is maintained there. In recent years, a strategy for transgene integration has been developed that uses cleavage with site-specific nucleases for targeted insertion into a chosen genomic locus. Nucleases specific for targeted genes (including "safe harbor" loci such as CCR5, CXCR4, AAVS1, albumin or Rosa) can be utilized such that the transgene construct is inserted by either homology directed repair (HDR) or by end capture during non-homologous end joining (NHEJ) driven processes. See, for example, U.S. Pat. Nos. 8,623,618; 8,034,598; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20060063231; 20080159996; 201000218264; 20120017290; 20110265198; 20130137104; 20130122591; 20130177983; 20130177960 and 20150056705, the disclosures of which are incorporated by reference in their entireties for all purposes. Nuclease-mediated integration offers the prospect of improved transgene expression, increased safety and expressional durability, as compared to classic integration approaches that rely on random integration of the transgene, since it allows exact transgene positioning for a minimal risk of gene silencing or activation of nearby oncogenes.

Engineered nucleases, including zinc finger nucleases, TALENs, CRISPR/Cas nuclease systems, and homing endonucleases designed to specifically bind to target DNA sites are useful in genome engineering and gene therapy. For example, zinc finger nucleases (ZFNs) and TALENs (including TALENs comprising Fok1-TALE DNA binding domain fusions, Mega TALs and cTALENs) are proteins comprising engineered site-specific zinc fingers or TAL-effector domains fused to a nuclease domain. Such nucleases have been successfully used for genome modification in a variety of different species at a variety of genomic locations. Additionally, clinical trials using engineered zinc finger nucleases have also demonstrated therapeutic utility (see, e.g. Tebas et at (2014) *New Eng J Med* 370(10):901).

These approaches have great potential for the treatment of diseases where the targeted gene product is considered un-druggable by small molecule approaches for a variety of reasons such as inaccessibility of the gene product or similarity with other essential gene products. Thus, there remains a need for the development of targeted fusion molecules (e.g. nucleases and transcription factors) for the prevention or treatment of diseases associated with the expression of disease-causing gene products.

SUMMARY

Disclosed herein are methods and compositions for altering the expression of one or more genes encoding proteins involved in a genetic disease (e.g., genes producing microRNAs; proteins lacking, deficient or aberrant in the disease and/or proteins that regulate these proteins). Alteration of such genes can result in the treatment of these genetic diseases. In particular, genome editing is used to knock out an aberrant gene, or change the expression of an endogenous gene. In other methods, genome editing is used to express a novel gene or gene variant to protect potentially susceptible cells, or to express an engineered protein and/or miRNA variant with novel and beneficial qualities. By way of non-limiting example, a mutated gene encoding alpha-1 antitrypsin (A1AT) may be corrected in a cell to produce a wild type protein or knocked out using a nuclease to treat A1AT deficiency. Other non-limiting examples of genes that may be targeted (including targeted inactivation or integration into such genes) include apolipoprotein B (APOB), angiopoietin-like protein 3 (ANGPTL3), proprotein convertase subtilisin/kexin type 9 (PCSK9), apolipoprotein C3 (APOC3), low density lipoprotein receptor (LDLR), C-reactive protein (CRP), apolipoprotein a (Apo(a)), Factor VII, Factor XI, antithrombin III (SERPINC1), phosphatidylinositol glycan class A (PIG-A), C5, alpha-1 antitrypsin (SERPINA1), hepcidin regulation (TMPRSS6), (delta-aminolevulinate synthase 1 (ALAS-1), acylCaA:diacylglycerol acyltransferase (DGAT), miR-122, miR-21, miR-155, miR-34a, prekallikrein (KLKB1), connective tissue growth factor (CCN2), intercellular adhesion molecule 1 (ICAM-1), glucagon receptor (GCGR), glucorticoid receptor (GCCR), protein tyrosine phosphatase (PTP-1B), c-Raf kinase (RAF1), fibroblast growth factor receptor 4 (FGFR4), vascular adhesion molecule-1 (VCAM-1), very late antigen-4 (VLA-4), transthyretin (TTR), survival motor neuron 2 (SMN2), growth hormone receptor (GHR), dystophia myotonic protein kinase (DMPK), cellular nucleic acid-binding protein (CNBP or ZNF9), clusterin (CLU), eukaryotic translation initiation factor 4E (eIF-4e), heat shock protein 27 (HSP 27), signal transduction and activator of transcription 3 protein (STAT3), vascular endothelial growth factor (VEGF), kinesin spindle protein (KIF11), hepatitis B genome, the androgen receptor (AR), Atonal homolog 1 (ATOH1), vascular endothelial growth factor receptor 1 (FLT1), retinoschism 1 (RS1), retinal pigment epithelium-specific 65 kDa protein (RPE65), Rab escort protein 1 (CHM), and the sodium channel, voltage gated, type X, alpha subunit (PN3 or SCN10A). One approach further involves the use of modification of a stem cell, which stem cell can then be used to engraft into a patient, for treatment of a disease.

In one aspect, described herein is a fusion molecule comprising a DNA-binding domain (e.g., ZFP, TALE, sgRNA, etc.) and a functional domain (e.g., cleavage domain, transcriptional activation domain, transcriptional repression domain, etc.) The fusion molecule may comprise an engineered nuclease (e.g., as a ZFN, a TALEN, a mega or homing endonuclease, a mega-TAL or a CRISPR/Cas system) that binds to target site in a region of interest in a genome, wherein the nuclease comprises one or more engineered domains. In one embodiment, the fusion molecule is a zinc-finger nuclease (ZFN) that cleaves a target genomic region of interest, wherein the ZFN comprises one or more engineered zinc-finger binding domains and a nuclease cleavage domain or cleavage half-domain. In certain embodiments, the fusion molecule (e.g., nuclease) binds to a target site in a gene that produces a microRNA (miRNA), for example an Mir-34 gene (e.g., a ZFP as shown in Table III). In another embodiment, the nuclease is a TALE nuclease (TALEN) that cleaves a target genomic region of interest, wherein the TALEN comprises one or more engineered TALE DNA binding domains and a nuclease cleavage domain or cleavage half-domain. In another embodiment, the nuclease is a CRISPR/Cas system wherein the specificity of the CRISPR/Cas is determined by an engineered single guide mRNA. Cleavage domains and cleavage half domains can be obtained, for example, from various restriction endonucleases and/or homing endonucleases. In one embodiment, the cleavage half-domains are derived from a Type IIS restriction endonuclease (e.g., Fok I).

In another aspect, described herein is a CRISPR/Cas system that binds to target site in a region of interest (e.g., a highly expressed gene, a disease associated gene or a safe harbor gene) in a genome, wherein the CRISPR/Cas system comprises a CRIPSR/Cas nuclease and an engineered crRNA/tracrRNA (or single guide RNA). In certain embodiments, the CRISPR/Cas system recognizes a target site in a highly expressed, disease associated, or safe harbor gene.

The ZFNs, TALENs and/or CRISPR/Cas system as described herein may bind to and/or cleave the region of interest in a coding or non-coding region within or adjacent to the gene, such as, for example, a leader sequence, trailer sequence or intron, or within a non-transcribed region, either upstream or downstream of the coding region. In some embodiments, the ZFNs, TALENs and/or CRISPR/Cas system binds to and cleaves a target gene. In another aspect, described herein are compositions comprising one or more of the zinc-finger, TALE or Cas nucleases as described herein.

In another aspect, described herein is a polynucleotide encoding one or more ZFNs, TALENs and/or CRISPR/Cas system as described herein. The polynucleotide may be, for example, mRNA. In some aspects, the mRNA may be chemically modified (See e.g. Kormann et al, (2011) Nature Biotechnology 29(2):154-157). In other aspects, the mRNA may comprise an ARCA cap (see U.S. Pat. Nos. 7,074,596 and 8,153,773). In further embodiments, the mRNA may comprise a mixture of unmodified and modified nucleotides (see U.S. Patent Publication 2012/0195936).

In another aspect, described herein is a ZFN, TALEN and/or CRISPR/Cas system expression vector comprising a polynucleotide, encoding one or more ZFNs, TALENs and/or CRISPR/Cas system described herein, operably linked to a promoter. In one embodiment, the expression vector is a viral vector.

In one aspect, described herein is a ZFN, TALEN and/or CRISPR/Cas system protein that is used to cleave a target DNA.

In yet another aspect, provided herein are cell lines and/or transgenic animal models (systems.) In some embodiments, the transgenic cell and/or animal includes a transgene that encodes a human gene. In some instances, the transgenic animal comprises a knock-out at the endogenous locus corresponding to exogenous transgene (e.g., the mouse globin gene is knocked out and the human globin gene is inserted into a mouse), thereby allowing the development of an in vivo system where the human protein may be studied in isolation. Such transgenic models may be used for screening purposes to identify small molecules or large biomolecules or other entities which may interact with or modify the human protein of interest. In some aspects, the transgene is integrated into the selected locus (e.g., safe-harbor) into a stem cell (e.g., an embryonic stem cell, an induced pluripotent stem cell, a hematopoietic stem cell, etc.) or animal embryo obtained by any of the methods described herein, and then the embryo is implanted such that a live animal is born. The animal is then raised to sexual maturity and allowed to produce offspring wherein at least some of the offspring comprise edited endogenous gene sequence or the integrated transgene.

In any of the methods described herein, the polynucleotide encoding the zinc finger nuclease(s), TALEN(s) and/or CRIPSR/Cas system can comprise DNA, RNA or combinations thereof. In certain embodiments, the polynucleotide comprises a plasmid. In other embodiments, the polynucleotide encoding the nuclease comprises mRNA.

In further aspects, the invention described herein comprises one or more gene-modulating transcription factors, such as a gene-modulating transcription factors comprising one or more of a zinc finger protein (ZFP TFs), a TALEs (TALE-TF), and a CRISPR/Cas-TFs for example, ZFP-TFs, TALE-TFs or CRISPR/Cas-TFs. In certain embodiments, the gene-modulating transcription factor can repress expression of a gene in one or more cells of a subject. The repression can be about 85% or greater, about 90% or greater, about 92% or greater, or about 95% or greater repression of gene in the one or more cells of the subject. In certain embodiments, the gene-modulating transcription factor can be used to achieve one or more of the methods described herein.

A kit, comprising the ZFPs, TALENs, ZFP-TFs, TALE-TF and/or CRIPSR/Cas nuclease or CRISPR/Cas TF system(s) of the invention, is also provided. The kit may comprise nucleic acids encoding the ZFNs, TALENs, ZFP-TF, TALE-TF, CRIPSR/CAS TF or CRISPR/Cas nuclease system, (e.g. RNA molecules or ZFP, TALEN or Cas9 encoding genes contained in a suitable expression vector) or aliquots of the proteins, and engineered sgRNA if needed, donor molecules, suitable host cell lines, instructions for performing the methods of the invention, and the like.

These and other aspects will be readily apparent to the skilled artisan in light of disclosure as a whole.

BRIEF DESCRIPTION OF THE DRAWINGS

FIG. 1A shows the Mir-34a locus found on Chromosome 1, while FIG. 1B shows the mir-34b and mir-34C loci on Chromosome 11.

FIG. 4A shows the activity of the mir-34A specific ZFN pair while FIG. 4B shows the activity of the mir-34c specific ZFN pair. Arrows depict the location of the mismatch band, and the percent NHEJ activity is indicated in the lanes.

DETAILED DESCRIPTION

Figure 1A:
FIGS. 1A and 1B depict the miR-34 loci.

Disclosed herein are methods and compositions for studying and treating a genetic disease. The invention describes genomic editing of one or more target genes such that there is a favorable change in the expression of one or more genes. The favorable change can result in prevention and/or treatment of a disorder in a subject in need thereof and/or the ability to study the disease in an animal model. Favorable changes in the expression of a gene includes, but is not limited, alteration of miRNA levels, silencing of an aberrant endogenous gene, or down regulation of an aberrantly expressed gene, up regulation of a regulatory gene or expression of a wild type version of an aberrant gene.

In certain embodiments, the target gene(s) are involved in lipid metabolism. Lipid metabolism disorders have great impact on human health. For example, hypercholesterolemia is a condition characterized by very high levels of cholesterol in the blood which is known to increase the risk of coronary artery disease. A large proportion of patients with hypercholesterolemia cannot achieve target desired low density lipoprotein (LDL) cholesterol levels with statin therapy, including genetic familial hypercholesterolemia patients, acute coronary syndrome patients, high-risk patient populations (e.g., patients with coronary artery disease, diabetics, symptomatic carotid artery disease, etc.) and other patients that are statin intolerant. Severe forms of hypercholesterolemia are estimated to affect more than 500,000 patients worldwide, and as a result, there is a significant need for novel therapeutics to treat patients with hypercholesterolemia whose disease is inadequately managed by existing therapies.

Fatty acids are emulsified in particles in the body, allowing them to be transported in the serum. There are several types of these particles, including chylomicrons, very low-density lipoprotein (VLDL), intermediate-density lipoprotein (IDL), low density lipoprotein (LDL) and high density lipoprotein (HDL) which are made up of variable protein and lipid constituents. For example, in the LDL particle, each particle contains a single apolipoprotein B-100 molecule, along with 80 to 100 additional ancillary proteins. Familial hypercholesterolemia, hyperlipidemia, and familial chylomicronemia are genetic conditions passed through families where an aberrant gene causes the observed symptomology. Mutations in genes encoding the LDL receptor (LDLR), Apoliprotein B (APOB), angiopoietin-like protein 3 (ANGPTL3) and proprotein convertase subtilisin/kexin type 9 (PCSK9) are involved in these diseases. The LDLR serves to remove LDL from the plasma for internalization into the cell. The LDLR is a transmembrane protein that localizes to clathrin-coated pits where it forms a complex with ApoB-100 (the longer gene product of APOB) and apoE enriched lipoproteins. Following endocytosis of this complex, it moves to the endosome where the lipoproteins are released from the complex for eventual degradation by the lysosome. The LDLR can then be recycled back to the cell surface.

Patients with defective apoB-100, termed 'Familial defective apoliprotein B' (FDB), frequently carry a R3500Q mutation in APOB which makes LDL with reduced ability to bind to the LDLR, reducing plasma clearance, thus raising plasma levels of fatty acids (Innerarity et al, (1987) *PNAS USA* 84:6919). FDB is generally recognized as an autosomal dominant condition, and occurs in approximately 1:700 people of European descent (Ginsburg and Willard (2012) *Genomic and Personalized Medicine*, volumes 1 and 2. Academic Press, London. p. 507). Thus, in FDB patients that are heterozygous for the mutation at apoB-100, specific knock out of the defective apoB-100 allele can cause correction of the disease.

Similarly, angiopoietin-like protein 3 (ANGPTL3) overexpression mutations that cause elevated levels of ANGPTL3 can cause hyperlipidemia in subjects. ANGPTL3 also acts as dual inhibitor of lipoprotein lipase (LPL) and endothelial lipase (EL), and increases plasma triglyceride and HDL cholesterol in rodents. ANGPTL3 is expressed primarily in the liver and secreted, and normally acts to increase plasma levels of triglycerides, LDL cholesterol and HDL cholesterol where it acts directly on the liver to regulate hepatocellular lipoprotein secretion and clearance (Musunuru et at (2010) *N Engl J Med* 363:23 p. 2220). Thus, the methods and compositions of the invention can be used to prevent or treat hyperlipidemia related to ANGPTL3 overexpression. Engineered nucleases of the invention can be used to knock out the gene in a subset of cells in the liver, reducing the overall level of angiopoietin-like protein 3 in the plasma. Alternatively or in addition, the engineered transcription factors of the invention can be used to repress expression of ANGPTL3 in the liver.

PCSK9 is another gene encoding a protein that plays a major regulatory role in cholesterol homeostasis. PCSK9 binds to the epidermal growth factor-like repeat A (EGF-A) domain of LDLR, and induces LDLR degradation. Autosomal dominant, toxic gain of function mutations in PCSK9 (e.g. S127R, P216L, D374Y and N157K) have been described and are associated with hyperlipidemia and Familial hypercholesterolemia (FH) as a result of an increased rate of LDLR degradation leading to a corresponding increase in plasma LDL cholesterol (Abifadel et at (2003) *Nat Gen* 34(2):154). In addition, loss of function PCSK9 mutations have been identified (e.g. Y142X, C679X and R46L) that cause an increase in hepatic LDLR levels, with an associated substantial decrease in the amount of plasma LDL cholesterol, leading to an 88% reduction in the incidence of coronary heart disease (Cohen et at (2003) *New Eng J Med* 354(12):1264). Thus the methods and compositions of the invention can be used to treat or prevent hyperlipidemia and/or FH. Engineered nucleases can be designed to knock out a PCSK9 gene comprising a mutation that is associated with a toxic gain of function. Additionally, a wild type PCSK9 gene may be knocked out in a number of cells in the liver to treat FH caused by mutations in other genes such as LDLR or APOB. Alternatively, engineered transcription factors can be used to repress expression from a mutant or wild type PCSK9 gene.

Familial chylomicronemia syndrome, or FCS, is characterized by extremely high levels of plasma triglycerides and lead to a number of health problems such as abdominal pain, enlargement of the liver and spleen and recurrent acute pancreatitis. In addition, there are subjects with high triglyceride levels that do not have FCS, but, due to the elevated triglycerides, have similar health issues. Apolipoprotein C3, or apo-CIII, encoded by the APOC3 gene, is a component of very low lipoprotein (VLDL), LDL, HDL and chylomicrons, and normally inhibits lipolysis by inhibiting lipoprotein lipase and hepatic lipase. Apo-CIII inhibits hepatic uptake of triglyceride-rich particles and can be elevated in patients with hyperlipidemia (Bobik, (2008) *Circulation* 118:702) and is an independent cardiovascular disease risk factor. Knocking out the APOC3 gene in mice results in animals with reduced plasma triglyceride levels as compared to normals (Maeda et al (1994) *J Biol Chem* 269(38):23610). Thus, the methods and compositions of the invention can be used to prevent or treat a subject with lipid metabolism disorders (e.g., familial hypercholesterolemia, hyperlipidemia, and familial chylomicronemia) by disruption or alteration of the expression of an APOC3 gene through use of engineered nucleases and/or transcription factors.

Accordingly, target genes involved in lipid metabolism include but are not limited to the genes described herein.

In other embodiments, the target gene(s) are involved in vascular diseases such as cardiovascular disease and coronary artery disease. Similar to the lipid metabolism disorders discussed above, coronary artery diseases can also be caused by specific genes. For example, C-reactive protein (CRP) is a protein produced in the liver that has been associated with inflammatory disease. It is an acute phase protein that binds to phosphocholine expressed on the surface of dead or dying cells where its job is to activate the complement system to help clear the cell. In chronic inflammatory disease, increased levels of CRP may exacerbate disease symptoms by contributing and amplifying an overall chronic inflammatory state. In addition, it has been shown in rat models that CRP increases myocardial and cerebral infarct size, which, when translated into human patients, may be predicative of a more negative prognosis following heart attack. When inhibitors of CRP are introduced into these rat models, infarct size and cardiac dysfunction are decreased (Pepys et at (2005) *Nature* 440(27):1217) Inhibition of CRP thus may be beneficial both in inflammatory diseases and in coronary artery disease. The methods and compositions of the invention may be used to cause targeted modulation of CRP expression, either through the use of gene disruption with an engineered nuclease or by down regulation of expression by use of an engineered transcription factor.

Plasma lipoprotein (Lp(a)) is a low density lipoprotein particle comprising Apolipoprotein(a) (apo(a)), and is also an independent risk factor for cardiovascular disease including atherosclerosis. Apo(a) contacts the surface of LDL through apoB-100, linked by a disulfide bond, and it has been reported that genetic polymorphisms associated with elevated Apo(a) levels are associated with an excessive rate of myocardial infarction (Chasman et at (2009) *Atherosclerosis* 203(2):371). Lp(a) concentration in the plasma varies widely in concentration between individuals, where these concentration differences appear to be genetically determined. The apo(a) gene comprises a number of plasminogen kringle 4-like repeats, and the number of these kringle repeats is inversely related to plasma concentration of Lp(a). A DNA-vaccine approach, designed to mount an immune response to apo(a) and cause antibody-mediated clearance of Lp(a), demonstrated a reduction in the proatherosclerotic activity of Lp(a) in mice (Kyutoku et at (2013) *Sci Rep* 3 doi:10.1038/srep1600). Thus the methods and compositions of the invention can be used to reduce the expression of the ApoA gene, resulting in a decrease in plasma concentration of Lp(a). This can be accomplished by selective knock out of the Apo(a) gene through use of an engineered nuclease, or through down regulation of Apo(a) gene expression through use of an engineered transcription factor.

Clotting disorders, often referred to as thrombophilia, can have ramifications in vascular diseases. The complex network of biochemical events regulating mammalian coagulation comprises 5 proteases (factors II, VII, IX, and X and protein C) that interface with 5 cofactors (tissue factor, factor V, factor VIII, thrombomodulin, and surface membrane proteins) to generate fibrin, which is the main component of a clot. A delicate balance exists between powerful endogenous procoagulant and thromboresistant forces to ensure the fluidity of blood and maintain the readiness of these factors to induce a blood clot if an injury occurs. High plasma activity of both Factor XI and Factor VII are associated with hypercoagulation and thrombotic disease (coronary infarcts, stroke, deep vein thrombosis, pulmonary embolism) and with poor patient prognosis. It has been demonstrated that people that with severe Factor XI deficiency are protected from ischemic brain injury and stroke (Saloman et at (2008) *Blood* 111:4113). At the same time, it has been shown that high levels of FXI are associated with higher rates of stroke incidents in patients (Yang et at (2006) *Am J Clin Path* 126: 411). Similarly, high Factor VII levels are also associated with coronary artery disease although this is complicated by other considerations such as how the Factor VII is measured, and which form of the protein is analyzed (Chan et at (2008) *Circulation* 118:2286). Thus, the methods and compositions of the invention can be used to prevent or treat subjects with hyperthrombotic disease through selective targeting of clotting factors associated with the disease (for example, Factor VII and Factor XI). Engineered nucleases may be used to knock out these genes in a subset of cells in the liver, or an engineered transcription factor may be used to down regulate their expression.

As described above, the balance of the clotting cascade is crucial. Thus, in addition to the importance of the clotting factors, the inhibitors of these factors are also critical. Patients with hemophilias are deficient in one or more components of the clotting cascade, and have a reduced clotting capacity as a consequence. In one of the last steps of this cascade, thrombin acts on fibrinogen to create fibrin which is the main component of the clot. The cascade leads up to the production of active thrombin to allow this to occur. To keep the system balanced, antithrombin (also known as antithrombin III, encoded by the SERPINC1 gene) acts upon thrombin to inhibit its action. In many hemophilias, the factor deficiency is not absolute and there is some degree of clotting that occurs. Thus an approach based on an inhibition of antithrombin could allow the clotting cascade to produce sufficient clotting when the upstream factors are limited, potentially regardless of which factor is deficient. This has been demonstrated using blood derived from hemophilia A patients (see Di Micco et at (2000) *Eur J Pharmacol.* March 10; 391(1-2):1-9.). The methods and compositions of the invention can used to treat patients with hemophilias such as Hemophilia A and Hemophilia B. Engineered nucleases as described herein can be used to treat or prevent hemophilias by selectively knocking out the SERPINC1 gene to allow more activity of the clotting cascade. In addition, or alternatively, selective transcription factors can be made to down regulate the expression of the SERPINC1 gene.

The target gene(s) may also be involved in blood disorders (hematological conditions). The complement system is a pivotal player in multiple hematological conditions. Paroxysmal nocturnal hemoglobinuria (PNH) is a hemolytic disease caused by a defect in the PIG-A gene (see Brodsky (2008) *Blood Rev* 22(2):65). The PIG-A gene product phosphatidylinositol glycan class A is required for the first step in the synthesis of GPI-anchored proteins. PIG-A is found on the X chromosome and mutations in PIG-A result in red blood cells that are sensitive to hemolysis by complement. Notably, these mutant cells lack the GPI-anchored proteins CD55 and CD59. CD59 interacts directly with the complement related membrane attack complex (or MAC) to prevent lytic pore formation by blocking the aggregation of C9, a vital step in the assembly of the pore. CD55 functions to accelerate the destruction of the C3 convertase, so in the absence of CD55, there is more of the C3 convertase enzyme, leading to more MAC formation. Thus, the lack of both of these proteins leads to increases lysis of the mutant red blood cells. For patients with PNH, complications due to increased thrombosis are the greatest concern (Brodsky (2008) *Blood Rev* 22(2):65). 40% of PNH patients have ongoing thrombosis which can lead to stroke and acute cardiovascular disease. Thus, the methods and compositions of the inventions can be used to treat and/or prevent PHN in a subject. A wild type PIG-A gene may be inserted into a safe harbor locus in a CD34+ cell derived from the subject such that the protein will be expressed during red cell development, producing cells that lack the sensitivity to complement.

Inhibition of the C5 component of complement has been approved as a treatment for both PNH and atypical hemolytic-uremic syndrome (aHUS), validating C5 as an important therapeutic target. The hemolysis of red blood cells associated with aHUS occurs when the cells are targeted for destruction by the alternative pathway due to a dysregulation of the complement system (part of innate immunity). Normally the destructive C3bBb complex is formed on the surface of an invading cell (e.g. a bacterium) to hasten its destruction as part of the alternative pathway in the complement system. The C3bBb complex can bind another C3b to form a C3bBbC3b complex which then acts as a C5 convertase. C5 convertase cleaves C5 to C5a and C5b, and C5b recruits C6, C7, C8 and C9 to form the MAC. A set of complement regulatory proteins (e.g. CD35, CD46, CD55 and CD59) are located on the body's own cells to inhibit the activity of these proteins and thus protect them. However, when there is an imbalance of these regulatory proteins, the C3bBb complex can form inappropriately (de Jorge et at (2011) *J Am Soc Nephrol* 22:137). This syndrome, in addition to the premature destruction of red blood cells can also lead to kidney disease as a result of the damaging and clogging of the glomerular filtering apparatus. C5 negative mice were shown to be protected when crossed with mice with complement regulator protein mutations, data that has been used to validate the idea of C5 as a target in aHUS (de Jorge, ibid) and other diseases related to complement dysregulation. In fact, the C5b-specific monoclonal antibody eculizamab has been successfully used to treat aHUS (Gruppo and Rother, (2009) *N Engl J Med* 360; 5 p 544) and other complement-mediated diseases (e.g. Paroxysmal Nocturnal Haemoglobinuria (PNH) (Hillmen et al, (2013) *Br. J Haem* 162:62)) Thus, the methods and compositions of the invention can be used to inhibit the expression of C5 and so prevent or treat diseases associated with complement dysregulation. For example, specific engineered nucleases may be used to knock out the C5 gene and/or specific transcription factors may be used to down regulate its expression.

Alpha-1-antitrypsin (A1AT) deficiency occurs in about 1 in 1500-3000 people of European ancestry but is rare in individuals of Asian descent. The alpha-1-antitrypsin protein is a protease inhibitor that is encoded by the SERPINA1 gene and serves to protect cells from the activity of proteases released by inflammatory cells, including neutrophil elastase, trypsin and proteinase-3 (PR-3). Deficiency is an autosomal co-dominant or a recessive disorder caused by mutant SERPINA1 genes in heterozygous individuals where reduced expression from the mutant allele or the expression of a mutant A1AT protein with poor inhibitory activity leads to chronic lack of inhibition of neutrophil elastase resulting in tissue damage. The most common SERPINA1 mutation comprises a Glu342Lys substitution (also referred to as the Z allele) that causes the protein to form ordered polymers in the endoplasmic reticulum of patient hepatocytes. These inclusions ultimately cause liver cirrhosis which can only be treated by liver transplantation (Yusa et at (2011) *Nature* 478 p. 391). The polymerization within the hepatocytes results in a severe decrease in plasma A1AT levels, leading to increased risk of this inflammatory disease. In addition, A1AT deficiency is linked to pulmonary diseases including chronic obstructive pulmonary disease (COPD), emphysema and chronic bronchitis (Tuder et at (2010) *Proc Am Thorac Soc* 7(6): p. 381) and potentially may have a far broader reach into the inhibition of the progression of other diseases including type 1 and type 2 diabetes, acute myocardial infarction, rheumatoid arthritis, inflammatory bowel disease, cystic fibrosis, transplant rejection, graft versus host disease and multiple sclerosis (Lewis (2012) *Mol Med* 18(1) p. 957). Population studies have suggested a minimum ATA1 plasma threshold of approximately 0.5 mg/mL (normal plasma levels are approximately 0.9-1.75 mg/ML in a non-inflammatory state) to avoid these diseases, and current therapies mostly act to reduce symptoms through the use of bronchodilators and the like, although the use of weekly infusions of A1AT (Zemaira®) is also an option for emphysema patients with a demonstrated severe lack of plasma A1AT. Severe lung disease associated with A1AT also is ultimately treated by transplant. Clinical trials for the treatment of A1AT deficiency involve a variety of approaches including the delivery of concentrated A1AT protein, use of an AAV construct comprising an A1AT gene by IM injection, and the use of A1AT in HIV, to list just a few. Thus, the compositions and methods of the invention can be used to treat or prevent diseases related to A1AT deficiency. Nucleases specific for the mutant A1AT allele (e.g. the Z allele) can be made to knock out the gene and prevent expression, thereby eliminating the hepatic aggregates that can lead to cirrhosis. Additionally, the mutant SERPINA1 gene may be corrected through the targeted donor delivery to alter the mutated sequence. Alternatively, or in addition, a wild type SERPINA1 gene may be introduced into a safe harbor locus for expression, or may be introduced into the albumin locus in vivo for increased hepatic secretion.

Another liver target of interest include any gene(s) that is(are) involved in the regulation of iron content in the body. Iron is essential for the hemoglobin production, but in excess can result in the production of reactive oxygen species. In patients that are dependent on blood transfusions (e.g. certain hemophilias, hemoglobinopathies), secondary iron overload is common. The iron-regulatory hormone hepcidin, and its receptor and iron channel ferroportin control the dietary absorption, storage, and tissue distribution of iron by promoting its cellular uptake. The regulation of hepcidin is done at a transcriptional level, and is sensitive to iron concentrations in the plasma where increased hepcidin expression leads to lower plasma iron concentrations. Through a series of receptor-ligand interactions, involving a receptor known as hemojuvelin, the hepcidin gene is upregulated by a SMAD transcription factor. Iron-related hepcidin down regulation in turn is regulated by a protease known as TMPRSS6, which cleaves hemojuvelin and prevents the upregulation of hepcidin (Ganz (2011) *Blood* 117:4425). Down regulation of TMPSS6 expression by use of an inhibitory RNA targeting the TMRSS6 mRNA has been shown to cause a decrease in iron overload in mouse models (Schmidt et al (2013) *Blood* 121:1200). Thus, the methods and compositions of the invention can be used to target TMPRSS6 and treat iron overload by use of an engineered nuclease to knock out the TMPRSS6 gene in a subset of cells in the liver, or through use of an engineered transcription factor to repress TMPRSS6 expression.

Other conditions related to iron utilization pathways in the body are porphyrias. These disorders result from a number of deficiencies in the enzymes involved in heme synthesis. Acute intermittent porphyia (AIP) is an autosomal dominant disorder and is the second most common porphyria, with an incidence of approximately 5-10 in 100,000 people. AIP is caused by a deficiency in hydroxymethylbilane synthase (HMB synthase (HMBS), also called porphobilinogen-deaminase), where the mutations in the HMBS gene are very heterogeneous, comprising missense and point mutations (Solis et al (1999) *Mol Med* 5:664). The potentially life-threatening AIP attacks can have gastrointestinal, neurophychiatric, cardiovascular and nervous system manifestations. Attacks have several triggers, can last for several days, and often require hospitalization and can be precipitated by several seemingly unrelated factors including certain drugs, infection, caloric restriction, smoking, alcohol and hormonal fluctuations relating to the menstrual cycle (Yasuda et al (2010) *Mol Ther* 18(1):17). HMB synthase is part of the heme synthesis pathway, where glycine and succinyl-CoA are joined by delta-aminolaevulinate synthase 1 (ALAS-1) to make aminolevulinic acid, which is then acted upon by aminolevulinic acid dehydratase (ALAD) to make phophobillinogen. Phosphobillinogen is the converted to hydroxymethylbilane by HMB synthase. The pathway continues on from there, ultimately producing the heme (Ajioka et at (2006) *Biochim Biophys Acta* 1762:723). Regardless of the trigger, all attacks result in an elevation of the enzyme delta-aminolevulinate synthase 1 (ALAS-1). This enzyme is the first enzyme in the hepatic heme synthesis pathway and when induced, the deficiency in HMB synthase becomes rate-limiting and the aminolevulinic acid and phospho-billinogen precursors accumulate (Yasuda, ibid). Liver transplant in AIP patients can stop the attacks, indicating that targeting the liver may be therapeutically beneficial. Additionally, in mouse models of AIP, where the mice have only 30% of normal HMB synthase levels, insertion of the transgene HMBS, encoding HMB synthase, resulted in a decrease in aminolevulinic acid and phosphobillinogen accumulation when the mice were given phenobarbital (Yasuda, ibid). Double stranded RNAs designed for the inhibition of ALAS-1 have also been shown to reduce ALAS-1 expression in vivo in a mouse AIP model and to reduce phosphobillinogen accumulation in response to phenobarbital treatment (see U.S. Patent Publication 20130281511). Thus the methods and compositions of the invention may be used to prevent and treat AIP. Insertion of a wild type HMB synthase transgene could treat pathologies relating to inadequate HMBS expression, and alternatively or in addition, down regulation of ALAS-1 expression through use of an engineered transcription factor could prohibit the toxic accumulation of aminolevulinic acid and phosphobillinogen. In addition, knock out of the ALAS-1 gene can accomplished using the engineered nucleases of the invention.

Non-alcoholic fatty liver disease (NAFLD) is the most common form of liver disease worldwide, with a prevalence of 15%-30% in Western populations and is caused by triglyceride accumulation within the liver. However, the prevalence increases to 58% in overweight populations and 98% in obese populations. Nonalcoholic steatohepatitis (NASH) is a more advanced form of NAFLD where liver injury has occurred, and can lead to liver failure, portal hypertension, hepatocarcinoma and cirrhosis (Schwenger and Allard (2014) *World J Gastronen* 20(7): 1712). Evidence appears to suggest that the hepatic triglyceride accumulation observed in NALFD is strongly associated with hepatic insulin resistance, often as a part of type 2 diabetes and metabolic syndrome (Choi et at (2017, *J Biol Chem* 282 (31): 22678). Acyl-CaA:diacylglycerol acyltransferase (DGAT) catalyzes the final step in triglyceride synthesis by facilitating the linkage of sn-1,2 diacylglygerol (DAG) with a long chain acyl CoA. There are two primary isoforms of DGAT, DGAT-1 and DGAT-2. DGAT-1 is primarily expressed in the small intestine while DGAT-2 exhibits primarily hepatic expression where its expression is insulin responsive. Knock down of expression of DGAT-1 or DGAT-2 using antisense oligonucleotides in rats with diet-induced NALFD significantly improved hepatic steatosis in the DGAT-2 knockdowns but not the DGAT-1 knockdowns (Choi, ibid). Thus, the materials and methods of the invention can be used to alter expression of DGAT-2 for the treatment of NASH and NALFD, and to reduce hepatic insulin resistance. Engineered nucleases can be used to knock out DGAT-2 in a subset of liver cells, or an engineered transcription factor can be used to down regulate DGAT-2 expression.

The target(s) may also be involved in viral infections. Approximately 170 million people worldwide are chronically infected with the hepatitis C virus (HCV). It is a major cause of liver cirrhosis, liver failure, and hepatocellular carcinoma and is the leading indication for liver transplant in many Western countries. It is treated currently with administration of pegylated interferon and ribavirin for 24 to 48 weeks, where such treatments can have substantial side effects, leading to poor patient compliance. Even putting aside the side effect issues, the cure rate for the use of pegylated interferon/ribavirin is less than 50% (Fried et at (2002) *NEJM* 347(13) p. 975). Thus, there is an urgent need for a more effective and cost efficient therapy for treatment or prevention of HCV.

In certain embodiments, the target gene(s) are involved in production of microRNAs. Micro RNAs are the products of a multistep biogenesis. Most primary miRNA transcripts are produced from Pol H-mediated transcription and are cleaved in the nucleus to make a pre-miRNA which is then transported to the cytoplasm. Once there, Dicer and its partner proteins excise the pre-miRNA loop, leaving a dsRNA comprising the mature miRNA strands. These are then bound by the proteins of the miRNA-induced silencing complex (miRISC) and guided to target sites in the 3' untranslated regions of mRNAs that the miRNAs act on (Gerbert et al, (2014) *Nuc Acid Res* 42 (1):609). The most abundant miRNA in the liver is miR-122, and it has been shown be play a role in liver cell identity, lipid metabolism and hepatitis C replication (Haussecker and Kay (2010) *Mol Ther* 18(2):240). miR-122 binds to two highly conserved target sites in the 5'-untranslated region of the HCV genome, forming a complex that protects the viral genome from nucleolytic degradation. Inhibition of miR-122 has also been associated with an improvement in steatosis in a mouse model of diet-induced obesity implying a role for miR-122 inhibition in non-alcoholic fatty liver disease. However, miR-122 also regulates several host genes that have been implicated in the development of hepatocellular carcinoma, suggesting that miR-122 also has tumor-suppressing activity (Janssen et at (2013) *NEJM* 368(18): 1685). Thus inhibition of miR-122 has the possibility of being affective for the treatment or prevention of Hepatitis C and non-alcoholic fatty liver disease, yet the loss of this miRNA may be associated with the development of hepatocellular carcinoma. Therefore, the methods and compositions of the invention may be useful for the prevention and or treatment of Hepatitis C through the use of a specific inhibitor of the transcription of the pre-miRNA that produces miR-122. Such a transcription factor would be engineered to down regulate expression without knocking out expression completely. This transcription factor could then be used to treat or prevent infection by Hepatitis C.

Hepatitis B remains a worldwide health threat despite the emergence of a large scale vaccination. Although both Hepatitis B and Hepatitis C infect the liver, the two viruses are dissimilar and are members of different viral families: Hepatitis B (HBV) is a double stranded DNA virus from the hepadnavirus family and Hepatitis C is a single stranded RNA virus from the flavivirus family. Chronic Hepatitis B (CHB) infections are one of the leading causes of death across the world and approximately 15-40% of people with CHB develop serious disease sequelae over their lifetime. 300 million people have CHB with 75% of infected individuals residing in the Asia Pacific region (Halegoua-De Marzio and Hann (2014) *World J Gastroenterol* 20(2):401). In Africa and East Asia, approximately 60% hepatocellular carcinoma (HCC) in patients is attributable to CHB, while in the developed Western world, approximately 20% of HCC is linked to CHB (Di Bisceglie (2009) *Hepatology* 49(5 Suppl): S56-S60). The exact nature of the link between HCC and CHB is not known but could be due to the chronic inflammation in the liver as a result of CHB, or as a direct result of the viral integration into the genome. There are currently six types of treatment available for CHB patients, including interferon and five nucleotide/nucleoside analogues (including lamivudine, adefovir, entecavir, tellbivudine and tenofovir). The aim of these treatments is to suppress HBV replication and thus patient adherence to the treatment regime is important (Halegoua-De Marzio and Hann, ibid). The HBV viral genome has been shown to integrate into the host genome, but this integration is not essential for its replication. However, it appears that integration of the HBV into the mixed-lineage leukemia 4 (MLL4) gene, resulting in an HBV caused upregulation of MLL4 expression, may be linked to the development of HCC (Jiang et at (2012) *Gen Res* 22: 593). Thus, the methods and compositions of the invention can be used to treat CHB infection and prevent or treat HCC. Engineered nucleases designed to knock out transcriptional activity in the integrated HBV virus, and thus prevent 'run-through' transcription into the adjacent human genes. HBV integration also appears to cause genome instability, resulting in alteration of nearby gene dosage following loss of segments of the genome (Jiang, ibid). Engineered nucleases of the invention, used in pairs, can be used to resect the virus from the genome, and thus treat HBV associated genome alteration. In addition, or alternatively, engineered transcription factors can be used to specifically repress HBV expression, and treat HBV infection.

Further vascular targets include those involved in hereditary angioedema (HAE). HAE is an autosomal dominant disease that affects 1 in 50,000 people and is a result of decreased levels of the C1 inhibitor. Patients experience recurrent episodes of swelling in any part of the body where swelling localized to the oropharynx, laryx or abdomen carry the highest risk of morbidity and death (see Tse and Zuraw, (2013) *Clev Clin J of Med* 80(5):297). The disease occurs from extravasation of plasma into tissues as a result of the over production of bradykinin. The mechanism seems to involve the cleavage of prekallikrein (also known as PKK) by activate factor XII, releasing active plasma kallikrein (which activates more factor XII). Plasma kallikrein then cleaves kininogen, releasing bradykinin. The bradykinin then binds to the B2 bradykinin receptor on endothelial cells, increasing the permeability of the endothelium. Normally, the C1 inhibitor (encoded by SERPING1) controls bradykinin production by inhibiting plasma kallikrein and the activation of factor XII. HAE occurs in three types, Type I and II that are distinguished by the amount and type of C1 inhibitor present, and Type III which is tied to a Thr309Lys mutation in factor XII (Prieto et at (2009) *Allergy* 64(2): 284). Type I HAE has low levels of C1 inhibitor that appear to be a result of poor expression and destruction of the small amount of C1 inhibitor protein that is made. Type 1 accounts for approximately 85% of HAE patients. Type II patients have normal levels of C1 inhibitor, but the C1 inhibitor protein is ineffectual due to mutations (Tse and Zuraw, ibid). More than 250 mutations in SERPING1 have been characterized that lead to Type I HAE including small and large insertions and deletions as well as duplications (Rijavec et at (2013) *PLoS One* 8(2): e56712). Due to this high variability in the genetic basis of HAE, the methods and compositions of the invention can be used to prevent or treat HAE by targeting downstream players in the manifestation of HAE. For example, targeting the gene encoding prekallikrein (KLKB1, expressed in hepatocytes) to effect a decrease in prekallikrein (abbreviated PKK) expression can result in a decrease in bradykinin production without regard to the type of mutation upstream that is causing the HAE, and thus result in a decrease in plasma extravasation. Thus, the methods and compositions of the invention may be used to cause a decrease in the expression of KLKB1 to prevent or treat HAE. Engineered nucleases can be used to knock out KLKB1 in a subset of hepatocytes that will reduce bradykinin production, and/or engineered transcription factors can be used to down regulate KLKB1 expression.

Target(s) may also be involved a fibrotic disease. Fibrotic disease in various organs is the leading cause of organ dysfunction and can occur either as a reaction to another underlying disease or as the result of a predisposition towards fibrosis in an afflicted individual. The hallmark of fibrosis is the inappropriate deposition of extracellular matrix compounds such as collagens and related glycoproteins. TGF-β plays a major role in the fibrotic process, inducing fibroblasts to synthesize extracellular matrix (ECM) proteins, and it also inhibits the expression of proteins with ECM break down activity (Leask (2011) *J Cell Commun Signal* 5:125). There is a class of ECM regulatory proteins known as the CNN proteins (so-called because the first three members are described, namely CYR61 (cysteine-rich 61/CCN1), CTGF (connective tissue growth factor/CCN2), and NOV (nephroblastoma overexpressed/CCN3). These proteins regulate a variety of cellular functions including cell adhesion, migration, apoptosis, survival and gene expression. TGF-β strongly upregulates the CCN2 expression which acts synergistically as a co-factor with TGF-β and seems to be involved in pericyte activation, a process which appears to be essential in fibrosis (Leask ibid). CCN2 is overexpressed in fibrotic tissue, including pulmonary tissue and is also found in the plasma of patients with systemic sclerosis (scleroderma). Also, knock down of CCN2 expression through use of antisense oligonucleotides (ASO) reduced chemical-induced liver fibrosis, ureteral obstruction-induced renal fibrosis, fibrotic scarring in cutaneous wounds, and renal interstitial fibrogenesis following partial nephrectomy (Jun and Lau (2013) *Nat Rev Drug Discov.* 10(12): 945-963). In addition to its pro-fibrotic role, CCN2 may be important in cancer, especially in metastasis. It may promote tumor growth by inducing angiogenesis, and high levels of CCN2 in breast cancer cells is a marker of bone metastasis potential (Jun and Lau, ibid). Experimental models that knock down CCN2 expression in various models of fibrosis, cancer, cardiovascular disease and retinopathy through the use of CCN2 modulating compounds such as monoclonal antibodies or inhibitory RNAs have shown impact of clinical progression of a number of these diseases. (Jun and Lau ibid). Thus, the methods and compositions of the invention can be used to prevent or treat fibrosis, cancer, vascular disease and retinopathy by decreasing expression from the CCN2 locus. Engineered nucleases can be designed to disrupt the CCN2 gene and cause a knockout of expression following error-prone healing of the DNA double-strand break (DSB) induced by the nuclease. Additionally, CCN2-specific engineered transcription factors may be used to repress CNN overexpression in diseased tissues. These treatments may be administered to scleroderma patients via introduction into the lung, or may be administered locally or systemically to treat cancer and vascular disease patients. Treatments may be administered locally or systemically for fibrosis patients.

In other embodiments, the target(s) are involved in an autoimmune disease. Autoimmune diseases as a class are common, and affect more than 23 million people in the United States alone. There are several different kinds with many different levels of severity and prognoses. Generally, they are characterized by the production of auto-antibodies against various self-antigens leading to an immune response against one's own body. Autoimmune disease of the gut can lead to conditions such as ulcerative colitis and inflammatory/irritable bowel disease (e.g. Crohn's disease). The cell surface glycoprotein intercellular adhesion molecule 1 (ICAM-1) is expressed on endothelial cells and upregulated in inflammatory states, serving as a binding protein for leukocytes during transmigration into tissues. Specific ICAM-1 alleles have been found to be associated with Crohn's disease (e.g. K469E allele, exon 6) or with ulcerative colitis (e.g. G241R,exon 4) and may preferentially participate in the chronic inflammatory induction found in these diseases (Braun et at (2001) *Clin Immunol.* 101(3): 357-60). Knock out of ICAM in mouse models of vascular and diabetic disease have demonstrated the usefulness of this therapeutic approach (see Bourdillon et at (2000) *Ather Throm Vasc Bio* 20:2630 and Okada et at (2003) *Diabetes* 52:2586, respectively). Thus, the methods and compositions of the invention may be used for the general reduction of ICAM expression in inflammatory diseases, or specific alleles associated with specific diseases may be targeted. For example, engineered nucleases can be used to knock out a mutant ICAM-1 allele in the gut, or engineered transcription factors can be used to down regulate these mutated genes.

Another common disease that has been more recently recognized as an autoimmune disease is diabetes. Glucagon, a peptide hormone released by the α-cell of pancreatic islets, plays a key role in regulating hepatic glucose production and has a profound hyperglycemic effect. In addition, glucagon activates multiple enzymes required for gluconeogenesis, especially the enzyme system for converting pyruvate to phosphoenolpyruvate, the rate-limiting step in gluconeogenesis. It has been proposed that hyperglucagonemia is a causal factor in the pathogenesis of diabetes based on the following observations: 1) diabetic hyperglycemia, from animal to human studies, is consistently accompanied by relative or absolute hyperglucagonemia; 2) infusion of somatostatin inhibits endogenous glucagon release, which in turn reduces blood glucose levels in dogs with diabetes induced by alloxan or diazoxide; and 3) chronic glucagon infusion leads to hepatic insulin resistance in humans (see Liang et at (2004) *Diabetes* 53(2):410). The glucagon receptor (encoded by the GCGR gene) is expressed predominantly in the liver, and treatment of diabetic (db/db) mice with antisense RNA targeting the glucagon receptor causes a significant reduction in serum glucose levels, triglycerides and fatty acids in comparison with controls (Liang et al, ibid). Similarly, glucocorticoids (GCs) increase hepatic gluconeogenesis and play an important role in the regulation of hepatic glucose output. In db/db mice, a reduction in glucortocoid receptor (GCCR) expression through the use of targeted antisense RNAs caused ~40% decrease in fed and fasted glucose levels and ~50% reduction in plasma triglycerides. (see Watts et at (2005) *Diabetes* 54(6):1846). Thus, the methods and compositions of the invention may be used to prevent or treat diabetes through targeting the expression of the glucagon receptor GCGR gene and/or the glucocorticoid receptor GCCR gene. Engineered nucleases may be used to knock out GCGR and/or GCCR in a subset of liver cells, and in addition, or alternatively, engineered transcription factors may be used to down regulate the expression of one or both of these genes.

Another potential target in type 2, insulin resistant diabetes is protein tyrosine phosphatase 1B (PTP-1B). Insulin resistance is defined as the diminished ability of cells to respond to insulin in terms of glucose uptake and utilization in tissues. One of the most important phosphatases regulating insulin signaling is the PTP-1B which inhibits insulin receptor and insulin receptor substrate 1 by direct dephosphorylation. Mice that are PTP-1B −/− (mutated at both alleles) are hypersensitive to insulin and resistant to weight gain on high fat diets (see Fernandez-Ruiz et at (2014) *PLoS One* 9(2):e90344). Thus this target may be useful for both diabetes treatment and obesity. Developing inhibitory small molecules specific for this enzyme is problematic because of the highly conserved active site pocket, but antisense oligonucleotides directed PTP-1B has been shown to reduce PTP-1B mRNA expression in liver and adipose tissues by about 50% and to produce glucose lowering effects in hyperglycemic, insulin-resistant ob/ob and db/db mice, experiments that were repeated in non-human primates (see Swarbrick et at (2009) *Endocrin* 150:1670). Thus, the methods and compositions of the invention can be used to target the PTP-1B gene and reduce its expression, leading to increased insulin sensitivity. Engineered nucleases specific for PTP-1B and/or engineered transcription factors can be used to target and reduce PTP-1B expression.

A high risk factor for developing type diabetes insulin resistant diabetes is obesity. Worldwide, more than 1 billion people are estimated to be overweight (body mass index (BMI)≥25 kg/m$^2$, and more than 300 million of these are considered obese (BMI≥30 kg/m$^2$), meaning that obesity is one of the greatest threats to public health today (Lagerros and Rössner (2013) *Ther Adv Gastroenterol* 6(1):77). Obesity is highly associated with co-morbidities such as insulin resistant type II diabetes, dyslipidemia, hypertension and cardiovascular disease. Treatment of obesity typically starts with modification of diet and exercise, but often with a decrease in caloric consumption, a parallel and confounding decrease in energy expenditure by the body is observed (Yu et al, (2013) *PLoS One* 8(7):e66923). Fibroblast growth factor receptor 4 (FGFR4) has been shown to have an anti-obesity effect in mouse obesity models. FGFR4 is mainly expressed in the liver, and it and its ligand FGF19 (in humans) regulate bile acid metabolism. FGFR4/FGF19 regulate the expression of cholesterol 7 alpha-hydroxylase and its activity. In addition, FGFR4 and FGF19 seem to be involved in lipid, carbohydrate or energy metabolism. Hepatic FGFR4 expression is decreased by fasting, and increased by insulin. FGFR4 null mice also show changes in lipid profiles in comparison with wild type mice in response to different nutritional conditions. Treatment of obese mice with FGF19 increased metabolic rate and improved adiposity, liver steatosis, insulin sensitivity and plasma lipid levels, and also inhibited hepatic fatty acid synthesis and gluconeogenesis while increasing glycogen synthesis. Anti-sense reduction of FGFR4 in obese mice also lead to reduced body weight and adiposity, improvement in insulin sensitivity and liver steatosis, and increased plasma FGF15 (the mouse equivalent of FGF19) levels without any overt toxicity (Yu et al, ibid). Thus, the methods and compositions of the invention can be used to treat obesity by reducing the expression of FGFR4. Engineered nucleases may be used to knock out FGFR4 in a subset of hepatocytes and/or engineered transcription factors specific for FGFR4 may also be used to down regulate its expression.

Multiple sclerosis (MS) is a chronic, disabling, autoimmune disease of the central nervous system that is characterized by inflammation, demyelination and axonal destruction. The flare ups associated with relapsing MS (occurring in 85-95 percent of patients) are thought to be tied to the entry of activated lymphocytes into the brain. Currently available treatments are only able to inhibit the rate of relapses by about 30%. Inflammatory responses induce the expression of vascular adhesion molecule-1 (VCAM-1) on the endothelium of the vasculature, and the adhesion of the lymphocytes to VCAM-1 is a necessary step that then allows the activated cells to pass through into the brain. VCAM-1 adherence by the lymphocytes is mediated by binding of very late antigen-4 (VLA-4, also known as α4β1 integrin) on the surface of the activated lymphocyte (Wolf et at (2013) *PLos One* 8(3): e58438). Disruption of this interaction has been the idea behind the therapeutic use of anti-VLA-4 specific antibodies and small molecule antagonists (Wolf et al, ibid). Thus, the materials and methods of the invention can be used to target VCAM-1 or VLA-4 expression in the brain to inhibit MS-associated flare ups in patients. Engineered nucleases may be used to knock out VCAM-1 and/or VLA-4 in the brain and/or engineered transcription factors specific for VCAM-1 and/or VLA-4 may also be used to down regulate its expression.

Another disease of interest is Cushing's disease/syndrome (CS). In this disease, patients have elevated serum levels of glucocorticoid due to increased expression by the adrenal gland. CS is an uncommon condition with an incidence rate between 1.8 and 2.4 patients/million per year. The most common cause of endogenous CS is an ACTH-producing pituitary adenoma, seen in ~70% of patients with CS. Cortisol-producing adrenal adenomas and ectopic ACTH-producing tumors are less common, each accounting for ~10-15% of cases. The first-line treatment for patients with pituitary derived CS is transsphenoidal pituitary surgery (TSS) and unilateral adrenalectomy for cortisol-producing adrenal adenoma. Unilateral adrenalectomy is curative in almost all patients with cortisol-producing adrenal adenoma and permanent adrenal insufficiency is rare. Conversely, hypopituitarism is common after TSS, with a range between 13 and 81% (see Ragnarsson and Johannsson (2013) *Eur J Endocrin* 169:139). In some patients however, surgical resection is not successful and so pharmacological treatment is indicated. One approach is to inhibit the activity of the hypercortisolemia by targeting the glucocorticoid receptor (GCCR), for example, using Mifepristone (also known as RU 486), a GCCR antagonist (see Johanssen and Allolio (2007) *Eur J Endocrin* 157:561). However, RU 486 has several other activities (most notably, induction of an abortion in pregnant patients). Thus, the methods and compositions of the invention may be used to target the GCCR specifically to avoid unwanted side effects. Engineered nucleases may be used to knock out GCCR in a subset of hepatocytes and/or engineered transcription factors specific for GCCR may also be used to down regulate its expression.

Transthyretin Amyloidoses (TTRA) is one of several degenerative diseases suspected to be linked to misfolded and aggregated protein (amyloids). Transthyretin (TTR) is a tetramer produced in the liver and secreted into the bloodstream that serves to transport holo-retinal binding protein. However, upon conformational changes, it becomes amyloidogenic. Partial unfolding exposes stretches of hydrophobic residues in an extended conformation that efficiently misassemble into largely unstructured spherical aggregates that ultimately before cross-β sheet amyloid structures (see Johnson et at (2012) *J Mol Biol* 421(2-3):183). TTRA can occur in patients in both sporadic and autosomal dominant inherited forms which include familial amyloid polyneuropathy (FAP) and familial amyloid cardiomyopathy (FAC). These inherited forms are usually earlier onset and relate to over 100 point mutations described in the TTR gene. Generally, the more destabilizing of the protein that the mutation is, the more likely it is to have some amount of amyloid pathology. The amyloid formed causes selective destruction of cardiac tissue in FAC or peripheral and central nervous tissue in FAP. Some new therapeutic strategies for treating these diseases such as inhibitory RNA strategies center on trying to decrease the amount of TTR to decrease the aggregation potential of the protein (Johnson et al, ibid). Thus the methods and compositions of the invention can be used to target specific TTR mutants, and/or target wild type TTR in an effort to reduce the quantity of the pathological forms of the TTR protein and/or to decrease TTR concentration in general. Engineered nucleases may be used to knock out TTR in a subset of hepatocytes and/or engineered transcription factors specific for TTR may also be used to down regulate its expression.

Muscular diseases can also be approached using the methods of the invention. Spinal muscular atrophy is an autosomal recessive disease caused by a mutation in the SMN1 gene which encodes the 'survival of motor neuron' (SMN) gene and is characterized by general muscle wasting and movement impairment. The SMN protein is involved in the assembly of components of the spliceosome machinery, and several defects in the SMN1 gene are associated with splicing defects that cause exon 7 of the mature mRNA to be specifically excluded. These defects are especially prevalent in spinal motor neurons, and can cause spinal muscular atrophy. The severity of SMN1 defects can be modified by a paralogue of SMN1 known as SMN2. The SMN2 gene sequence differs from SMN1 in only a few single nucleotide polymorphisms in exons 7 and 8 and several others in the intronic sequences. However, during maturation of the mRNA transcribed from the SMN2 sequence, 90% of the time splicing occurs which also specifically excludes exon 7. Thus, alteration of the sequence in the SMN2 intron immediately upstream of exon 7 to remove the sequences tied to exon 7 exclusion will result in splicing where the exon is now included in the mature mRNA. This will allow SMN2 to replace a variety of defective SMN1 genes. Thus, the methods and compositions of the invention can be used to change the sequence at the defective splicing signal in SMN2 and cause a mature mRNA to be made that will result in the complementation of the SMN1 defects. Gene editing of SMN2 can be done using an engineered nuclease of the invention in combination with a specific oligonucleotide comprising the altered sequence such that following targeted cleavage of SMN2, the corrective oligonucleotide sequence will replace the sequence via HDR.

Dysregulation of the secretion of growth hormone (GH) can lead to a condition known as acromegaly, a disorder of disproportionate skeletal, tissue, and organ growth which first becomes evident at about 40 years of age (Roberts and Katznelson (2006) *US Endocrine Disease:* 71). It occurs an annual incidence of approximately 5 cases per million, and diagnosis requires a determination of dysregulation of GH secretion and elevated IGF1 levels. The inability to suppress GH secretion during the 2 hours post an oral glucose load is generally used for diagnosis of acromegaly. Normal regulation of GH secretion is carried out by the pituitary gland. Hypothalamic GH-releasing hormone (GHRH), ghrelin and somatostatin regulate GH production by anterior pituitary somatotroph cells. The gene encoding the GH receptor or GHR is widely expressed and when a GH molecule interacts with a GHR dimer, signal proceeds via JAK2-dependent and independent intracellular signal transduction pathways (see Melmed (2009) *J Clin Invest* 119(11):3189). Circulating GH stimulates hepatic secretion of insulin-like growth factor-1 (IGF-1). Acromegaly occurs when benign pituitary tumors cause an increase in GH secretion and thus in IGF-1 secretion. One GHR mutation that is tied to acromegaly has an in-frame deletion in exon 3 that causes a deletion of 22 amino acids in the protein. This mutated receptor, known as d3-GHR, results in enhanced GH responsiveness. Current therapies focus on the normalization of GH and IGF-1 levels, often through surgical removal of the pituitary tumors. Since secretion of IGF-1 is induced by GH, targeting of the GHR is an attractive target for the methods and compositions of the invention. Decreased expression as a result of knock out using engineered nucleases or down regulation of the GHR gene using engineered transcription factors will result in a lower density of GH receptors and may be used for the treatment or prevention of acromegaly.

Another disease associated with muscle wasting is myotonic dystrophy, which is a chronic disease characterized by muscle wasting, cataracts, heart conduction defects, endocrine changes, multiorgan damage and myotonia (prolonged muscle contraction following voluntary contraction). Myotonic dystrophy occurs at an incidence rate of approximately 13 per 100,000 people, and there are two forms of the disease, Myotonic Dystrophy Type 1 (also called Steinert's disease, MMD1 or DM1, and is the most common) and Myotonic Dystroply Type 2 (MMD2 or DM2). Both are inherited autosomal dominant diseases caused by abnormal expansions in the 3' non-coding regions of two genes (CTG in the DMPK gene (encoding dystrophia myotonica protein kinase) for type 1, and CCTG in the ZNF9 gene (encoding cellular nucleic acid-binding protein) in type 2) and DM1 is the most common form of muscular dystrophy in adults. These mutations result in toxic intranuclear accumulation of the mutant transcripts in RNA inclusions or foci (see Caillet-Boudin et al, (2014) *Front. Mol. Neurosci doi:*10.3389). Type 1 patients have CTG copy numbers greater than 50 and have variable phenotypes, ranging from asymptomatic to severe. Antisense RNA techniques have been used to cause the specific destruction of the mutant DMPK transcripts in vitro which caused no effect on the proliferation rate of DM1 myoblasts but restored their differentiation (Furling et at (2003) *Gene Therapy* 10:795). Thus, the methods and compositions of the invention can be used to target the DMPK mutant genes or the ZNF9 gene to cause a decrease in the production of the mutant mRNAs. Engineered nucleases may be used to knock out these genes in myocytes and/or engineered transcription factors may also be used to down regulate their expression.

Cancer may also be targeted as described herein. Cancer is a generic term used to describe a number of specific diseases that are united by a lack of cellular growth regulation. Since there are so many forms, involving a myriad of different cell types, there are also numerous specific gene targets that are involved in cancer. For example, the clusterin protein (also known as apolipoprotein J), encoded by the CLU gene, is a heterodimeric protein assembled following the proteolytic cleavage into the two chains of the primary polypeptide CLU gene product. In recent years, it has been found that there are two forms of clusterin, a secretory and heavily glycosylated form (sCLU) and a nuclear form (nCLU), where nCLU is first synthesized as a pre nuclear form (pnCLU) that is found in the cell cytoplasm. The differences between the two CLU forms are tied to alternative splicing of the CLU message and the selection of the starting ATG during message translation. The translation of sCLU utilized the first AUG in the full length CLU mRNA whereas the translation of pnCLU is initiated from a second inframe AUG following the splice-dependent removal of the transcribed leader section and Exon 1 from the full length mRNA. The sCLU form appears to promote cell survival while the nCLU form is associated with apoptosis. Overexpression of the sCLU form of the protein has been found in many tumor types, including prostate, skin, pancreatic, breast, lung, and colon tumors, as well as oesophageal squamous cell carcinoma and neuroblastoma. In addition, the progression of some cancer types towards high grade and metastatic forms leads to an elevation of sCLU levels (Shannan et at (2006) *Cell Death Dif* 13: 12). Use of specific antisense oligonucleotides (ASO) designed to cause silencing sCLU expression in combination with standard treatments has been carried out in Phase I studies of breast and prostate cancer, with an increase in apoptosis observed only in the patients that received both the ASO and the standard therapeutic agent (Shannan ibid). Thus, the methods and compositions of the invention can be used to treat cancers marked with an increase in sCLU expression. Engineered nucleases of the invention can be designed to knockout the portion of the CLU gene encoding the initial ATG start site, forcing translation to initiate at the second AUG associated with the nCLU form.

Another protein that appears to have an oncogenic role is eukaryotic translation initiation factor 4E (eIF-4E). eIF3-4E binds to the M7GpppN cap (where N is any nucleotide) of a eukaryotic mRNA and is the rate limiting member for the formation of the eIF-4F complex. eIF-4E normally complexes with eIF-4G in the eIF-4F complex, and under normal physiologic conditions, the availability of eIF-4E is negatively regulated by the binding of a family of inhibitory proteins known as 4E-BPs which act to sequester eIF-4E from eIF-4G. Since eIF-4E is expressed normally at low levels, mRNAs compete for the available eIF-4E to be translated. mRNAs with short, unstructured 5' UTRs are thought to be more competitive for translation since they are less dependent on the unwinding activity found in the eIF-4F complex. mRNAs that are highly structural then are more dependent on eIF-4E binding for translation, and thus when eIF3-4E is overexpressed, these mRNAs are more easily translated. Growth-promoting gene products such as cyclin D1, VEGF, c-myc, FGF2, heparanase, ODC and MMP9 have these complex 5' UTRs (Mamane et at (2004) *Oncogene* 23:3172, Fisher (2009) *Cell Cycle* 8(16):2535). Additionally, eIF-4E may serve a role in modification of the nuclear pore complex and cause an increase in translocation of these same mRNAs into the cytoplasm (Culjikovic-Kraljacic et at (2012) *Cell Reports* 2 p. 207). eIF-4E has been implicated in oncogenic cellular transformation and is overexpressed in several cancer types including acute myeloid leukemia, colon, breast, bladder, lung, prostate, gastrointenstinal tract, head and neck cancers, Hodgkin's lymphoma and neuroblastoma and elevated levels are associated with increasing grade of disease. Targeting of eIF-4E has been attempted by several different approaches, including overexpression of 4E-BPs and peptides derived there from, the development of small molecule inhibitors to prevent eIF-4E:eIFG interaction, and antisense oligos (ASO) specific for eIF-4E (Jia et at (2012) *Med Res Rev* 00, No. 00:1-29). ASO administration has demonstrated a knock down of eIF-4E expression in tumor cells in vitro, and in xenograft tumors in mouse models in vivo. Expression levels of eIF-4E were decreased by 80% in these mouse models without any decrease in overall protein translation and without any obvious toxicity, while increasing chemosensitivity to chemotherapeutic agents, increasing cancer cell apoptosis and suppressing tumor growth (Jia ibid). Thus, the methods and compositions of the invention may be used for the treatment or prevention of various cancers. Expression of eIF-4F can be knocked-out through treatment with engineered nucleases, or expression of the gene may be down regulated by treatment with an engineered transcription factor. Further, inhibitory proteins such as the 4E-BPs may be overexpressed using the methods and compositions of the invention. Expression of these proteins may be increased using an engineered transcription factor, or the gene encoding a 4E-BP may be inserted by targeted integration into a site in the genome where it will be more highly expressed, either by utilizing an endogenous promoter at the insertion site, or by inserting the 4E-BP gene sequence linked to a strong promoter at a safe harbor locus.

Vascular endothelial receptor (VEGF), acting via its receptor VEGFR has a role in normal development, and also in the development of pathological angiogenesis in cancer. In humans, there are five distinct VEGF family members: VEGF-A (also known as VEGF); placenta growth factor (PIGF), VEGF-B, VEGF-C and VEGF-D. VEGF-A also has three common subtypes: VEGF-121. VEGF-165 and VEGF-189. The various VEGFs have differing roles in angiogenesis with VEGF-A primarily being involved in normal angiogenesis and also in tumor growth and metastasis, while VEGF-C and VEGF-D are involved in normal lymphangiogenesis and in malignant lymph node metastasis. In addition, the VEGF-A subtypes may also have specific growth promoting activity in hormone responsive tumors. Based on this knowledge, a number of antibodies and small molecule kinase inhibitors which suppress the VEGF-VEGFR interaction directly or the signal transduction pathways activated by the interaction. However, these therapeutics often have significant and potentially troublesome side effect profiles, such that active research is occurring to develop inhibitors with increased specificity (Shibuya, (2014) *Biomol Ther* 11(1):1-9). Thus, the methods and compositions of the invention may be used to prevent or treat cancer in a subject. Engineered nucleases can be made to target specific VEGF encoding genes (e.g. VEGF A, VEGF D) or to target specific VEGF A subtypes via the knockout of alternative splicing sequences. In addition, or alternatively, VEGF genes may be repressed by engineered tissue factors (e.g. ZFP-TF or TALE-TF).

Another protein that plays a role in several cancers is kinesin spindle protein (KSP), encoded by the KIF11 gene. The most successful anti-cancer therapies currently in use target microtubules where these agents have been used for the treatment of breast, lung, ovarian, bladder, and head and neck cancers. Microtubules are part of the mitotic spindle, and thus targeting them is successful in inhibiting rapidly dividing cancer cells, but microtubules are also part of the cytoskeleton, such that treatment with these agents also is associated with serious side effects. Kinesin, specifically kinesin spindle protein, is a motor protein that binds to spindle fibers and serves to force the spindle fibers apart during chromosome segregation in cell division. Thus, targeting KSP using a KSP-specific anti-mitotic agent will only target dividing cells, and might have fewer side effects. Agents that deplete KSP selectively lead to cell cycle arrest in mitosis, which after a prolonged period, leads to apoptosis. KSP is also abundant in dividing tissues, and is highly expressed in tumors of the breast, colon, lung, ovary and uterus (Sarli and Giannis, (2008) *Clin Cancer Res* 14:7583). In addition, clinical trials are underway using RNA interference targeted to KSP and VEGF simultaneously in cancer patients with liver involvement (Tabemero et al, (2013) *Cancer Discovery* 3:406). Thus, the methods and compositions of the invention may be used to treat or prevent cancers. Engineered nucleases can be targeted to the KIF11 gene to knock it out in tumor tissues. In addition or alternatively, engineered transcription factors can be used to repress expression of the KIF11 gene and cause the tumor cell to go into cell cycle arrest and eventually apoptose.

Heat shock protein 27 (HSP 27, also known as heat shock protein beta-1 or HSPB1) is another protein that is implicated in cancer. HSP 27, encoded by the HSPB1 gene, is a heat shock protein that was initially characterized in response to heat shock as a small chaperonin that facilitates proper refolding of damaged proteins. However, ongoing investigation revealed that it also is involved in responses to cellular stress conditions such as oxidative stress, and chemical stress, appears to have anti-apoptotic activity, and is able to regulate actin cytoskeletal dynamics during heat shock and other stress conditions (Vidyasagar et at (2012) *Fibrogen Tis Rep* 5(7)). In addition, suppression of HSP 27 may play a role in long term dormancy of cancers as research has revealed that HSP 27 is upregulated in angiogenic breast cancer cells, and suppression of HSP 27 in vivo leads to long term tumor dormancy (Straume et at (2012) *Proc Natl Acad Sci USA* doi/10.1073/pnas.1017909109). Increased expression of heat shock proteins in tumor cells is related to loss of p53 functions and to the upregulation of proto-oncogenes such as c-myc. HSP 27's anti-apoptotic activity protects tumor cells and also has been shown to be associated with chemotherapy resistance in breast cancer and leukemia (Vidysagar ibid). Thus, HSP 27 may be a suitable target for cancer therapeutics, where inhibitors of the protein may be used in combination with known chemotherapies to enhance their activities. The HSP 27 inhibitor quecertin has been shown to significantly reduce tumor volumes in vivo when combined with traditional chemotherapeutic agents in comparison with the agents alone. In addition, HSP 27 inhibitory ASOs are currently be evaluated in clinical studies in lung, ovarian, breast and pancreatic cancers (Vidyasagar, ibid). Thus, the methods and compositions of the invention may be used to treat cancers by inhibition of HSP 27 expression. The expression of HSP 27 may be knocked out by treatment of tumors or patients in need with engineered nucleases designed to cleave the HSPB1 gene. Alternatively, expression may be down regulated by treatment with an engineered transcription factor designed to repress expression from HSPB1. Further, expression may be down regulated by expression of a HSPB1-specific ASO inserted by targeted integration into the genome of a tumor cell.

Several kinases have been the target of research into anti-cancer therapeutics since they are often key regulators of cell growth. However, downstream in the signaling pathway, the effect of mutant kinases is often seen in the upregulation of the Signal Transduction and Activator of Transcription 3 protein, or Stat3, encoded by the STAT3 gene. Additionally, it appears that both Hepatitis B and C activate Stat3, and both are associated with the development of hepatic cancer. Thus it may be that the HepB and HepC viruses subvert Stat3 signaling pathways and promote hepatocyte transformation (Li et al, (2006) *Clin Cancer Res* 12(23):7140).

All the various Stat proteins are transcription factors that primarily mediate signaling from cytokine and growth factor receptors. For example, IL6 and IL11 bind to their respective receptor subunits and trigger homodimerization of gp130, the transmembrane receptor that triggers Stat3 activation. Following activation via phosphorylation of the growth factor receptors, Stat3 proteins dimerize and traverse into the nucleus and bind to DNA in a sequence specific manner, up regulating many genes that are involved in cell proliferation. Tumor cells of various types often have kinase mutations that lead to overexpression of Stat3 so a decrease in Stat3 expression has the potential to be beneficial in cancers of multiple origins without regard to each specific mutant kinase (Jarnicki et at (2010) *Cell Div* 5:14). Stat3 contributes to malignancy by several mechanisms. It inhibits apoptosis by upregulating the pro-survival/anti-apototic Bcl2 proteins and promotes proliferation primarily by stimulating expression of cyclinB1, cdc2, c-myc, VEGF, H1F1α and cyclin D1 as well as through its repression of the cell cycle inhibitor p21. Stat3 also promotes tumor metastasis through the induction of extracellular matrix-degrading metalloproteinases including MMP-2 and MMP-9. In normal physiological states, Stat3 functioning is inhibited by the transcriptional inhibitor Socs3, which is normally induced by Stat3 to maintain growth balance in the cell. However in a malignant cell, Stat3 overexpression can overcome Socs3 inhibition. Thus, the methods and compositions of the invention can be used to inhibit Stat3 functioning and prevent or treat cancer. Expression from STAT3 can be repressed using the engineered transcription factors of the invention. Additionally, STAT3 may be knocked out using an engineered nuclease of the invention to prevent Stat3 expression. The Socs3 transcriptional inhibitor can also be up regulated or overexpressed to control Stat3 expression.

Prostate cancer (PCa) is an androgen-dependent disease that remains one of the leading causes of death in the United States, and is the leading cause of death from cancer in men. While several studies have been done that suggest that up to 42% of prostate cancer cases have a genetic link (Mazaris and Tsiotras (2013) *Nephro Urol Mon* 5(3):792-800), several types of inheritance patterns have been observed (e.g. X-linked, autosomal dominant, autosomal recessive) suggesting that there is not one sole gene or gene mutation that leads to inheritance of PCa. This cancer is dependent upon the activity of the androgen receptor for growth and progression (Mahmoud et at (2013) *PLoS One* 8(10): e78479). Typically, PCa can be a slow to progress disease that can be treated using fairly conservative approaches, but in about 25-30% of the cases, the cancer can be an aggressive one leading to patient death. In the case of metastatic disease 70-80% of patients respond initially to androgen-deprivation therapy but in later stages, the tumor becomes hormone refractory and more aggressive, leading to a worsening prognosis (Mazaris and Tsiotras ibid). Hormone refractory PCa is not dependent on circulating androgen, but rather is driven by inappropriate activation of the androgen receptor (AR, encoded by the AR gene) through such mechanisms as AR amplification, deregulation of growth factors, and co-amplification of AR co-factors. Additionally, mutations in the AR ligand binding domain can cause the AR to be supersensitive to very low circulating androgen levels or to be sensitive to an expanded set of ligands such as estrogens, progestins, adrenyl steroids and antiandrogens. Tumor cells that have undergone these types of mutations in the AR ligand binding domain may no longer be sensitive to anti-androgen therapies despite the reliance of the cancer on the activity of the AR. Normally the AR is present in the cytoplasm and is bound by heat shock proteins to prevent its activation. Upon exposure to androgen, the receptor is able to dimerize and travel into the cell nucleus to promote expression of several growth related genes. Thus the methods and compositions of the invention may be used to treat PCa at all stages. Engineered nucleases of the invention can be made to knock out the AR gene in PCa cells, or engineered transcription factors may be used to down regulate its expression. Down regulation, either through gene knock out or transcriptional repression will deprive the tumor cells of the growth factor signaling pathways that these tumors are dependent on and thus treat or prevent a prostate cancer.

Another micro RNA that may play a role both in cancer and in scleroderma is miR-21. MiR-21 was one of the first mammalian microRNAs identified, and it is encoded by the MIR21 gene which is located in an intronic region of the TMEM49 gene. MIR21 has its own promoter and is transcribed in a 3400 nucleotide primary transcript that is subsequently edited into a short RNA duplex in the cytoplasm (Patel and Noureddine (2012) *Curr Opin Nephrol Hypertens* 21(4):410). In scleroderma patients, the expression of miR-21 correlated with scleroderma fibrosis (Zhu et at (2012) *J Clin Immunol* 32(3):514). miR-21 has also been shown to be upregulated in glioblastoma where it was expressed at a 5- to 100 fold higher rate than in normal tissue (Esquela-Kerscher and Slack (2006) *Nat Rev* 6: 259). It is also upregulated in several other cancers including breast, esophageal, gastric, colorectal, and lung cancer (Yang et al, (2013) *Biomed Rep* 1:495). miR-21 appears to be an 'oncomir' where it acts by inhibiting apoptosis, but does not appear to affect cell proliferation. Another potential oncomir is miR-155, which is linked with Myc overexpression and B-cell cancers. miR-155 is encoded in the BIC gene. It has been shown to be upregulated by 100 fold in pediatric Burkitt's lymphoma and Hodgkin's lymphoma, as well as primary mediastinal and diffuse large B-cell lymphomas. It has also been demonstrated to be upregulated in breast carcinoma (Esquela-Kerscher and Slack, ibid). Another miR of interest is miR-34a, which was found to be upregulated in renal cell carcinoma (Cheng et al (2013) *Oncol Let* 6:769). Interestingly enough, miR-34a was also found to be upregulated in brain tissue following prolonged (longer than 5 minute) seizures which cause damage to brain regions such as the hippocampus, as part of the pathophysiological response to these long seizures in epilepsy (Henshall (2013) *Front Mol Neurosci* 6:37).

Thus, the methods and compositions of the invention may be used to target one or more gene(s) of interest, including miR genes. Engineered nucleases can be made to knock out the expression of the gene (e.g., miR precursor) of interest. Alternately, or in addition to, engineered transcription factors can be used to down regulate the expression of pathological miRs in specific tissues to prevent or treat a disease.

The methods and compositions of the invention can also be used to target genes involved in hearing. The gene Atonal homolog 1 (Atoh1) is a basic helix-loop-helix transcription factor that is essential for inner ear hair cell differentiation. Hair cells transform sound and balance signals into electrical impulses in the cochlear and vestibular end organs. There is no effective way to stimulate their regeneration in mammals once hair cells have been damaged by noise, ototoxic drugs or aging, which hampers the treatment of neural hearing impairment that is caused by hair cell loss. Studies done with cultured cochlear tissues have shown that delivery of Atoh1 via AAV lead to the proliferation of ectopic hair cell-like cell in vitro (Luo et at (2014) *Mol Med Rep* 10(1): 15-20). Thus, the methods and compositions of the invention can be used to deliver transcript factors specific for the Atoh1 gene to induce expression of this gene and drive the production of additional inner ear hair cells in subjects with hearing loss due to damaged inner ear hair cells.

Optimal phototransduction requires separation of the avascular photoreceptor layer from the adjacent vascularized inner retina and choroid. Age related macular degeneration (AMD) is the leading cause of blindness in industrial nations, and is caused by neovascularization within the back of the eye such that the macula becomes occluded. Neovascularozation is driven in part by the effects of VEGF, and in a healthy eye, VEGF is kept in check by a soluble VEGF receptor sFLT-1. This protein is synthesized in the photoreceptors and retinal pigmented epithelium (RPE) cells. It has been demonstrated that AMD patients have reduced levels of sFLT-1 and in animal models of AMD, antibodies against the sFLT-1 protein and expression of RNAi molecules designed to decrease the expression of sFLT-1 caused ocular neovascularization (Luo et al. (2013) eLife 2:e00324. DOI: 10.7554/eLife.00324). Thus, the methods and compositions of the invention may be used to prevent or treat AMD.

Specific transcription factors designed to upregulate the FLT-1 gene will cause an increase in sFLT-1 receptor and inhibit the actions of VEGF on the eye. Genes encoding these transcription factors may be introduced directly into the eye for incorporation into the photoreceptor and RPE cells. In addition, nucleases specific for the VEGF gene may be used to knock out VEGF expression in the eye. VEGF knock out in the eye would result in the reduction of the angiogenesis and vascularization associated with AMD. Another form of blindness occurs in boys and is related to the X-linked gene RS1 (also known as retinoschisin 1). This gene encodes a secreted cell adhesion protein that is essential for maintaining the organization of the layers of the retina, and mutations in RS1 lead to retinoschisis, characterized by splitting of the retinal layers and early onset macular degeneration. It has been shown that introduction of AAV comprising the RS1 gene led to a rescue of the retinoschisis phenotype in RS1 knock-out mice (Byrne et at (2014) *Gene Ther* 21(6): 585-592). Thus the methods and compositions of the invention can be used to prevent or treat retinoschisis. Specific nucleases can be co-introduced into the eye, either as mRNAs or expression cassettes, with a wild type RS1 gene. The wildtype gene can be integrated into the genome of the photoreceptor cells via targeted integration into a safe harbor locus such as AAVS1 or CCR5. Alternately, a fragment of the RS1 gene may be introduced into the RS1 gene downstream of the promoter region such that the wildtype sequences are integrated into the endogenous locus and the gene is regulated by the endogenous RS1 promoter.

Leber congenital amaurosis (LCA) is the most severe retinal dystrophy causing blindness before the age of 1 year. LCA is a clinical syndrome as there are 22 different genetic mutations associated with the gene (Chacon-Camacho and Zenteno (2015) *World J Clin Cases* 3(2):112-124). Patients with LCA2 are a subset (approximately 6-16%) of all LCA patients and are characterized by mutations in the RPE65 gene. RPE65 is normally highly expressed in RPE cells and encodes the isomerohydrolase involved in the conversion of all-trans retinol to 11-cis retinal during phototransduction, which is then used in visual pigment regeneration in photoreceptor cells. Gene therapy studies have been done where a wild type RPE65 gene is delivered in the eye in an AAV vector and some restoration of sight was achieved (Al-Saikhan (2013) *Saudi J Ophthal* 27:107-111). Thus, the methods and compositions of the invention may be used to prevent or treat LCA2 by introduction of a wild type RPE65 gene into RPE cells. The gene may be introduced into a safe harbor locus such AAVS1 or CCR5 by co-delivery of the RPE65 gene and specific nucleases, delivered either as mRNAs or expression vectors. A fragment of the RPE65 gene may be also inserted into the RPE65 gene via targeted integration such that the wild type sequence is restored and the gene is under the control of the endogenous promoter.

Choroideremia is an x-linked condition characterized by progressive vision loss that is associated with the CHM gene, and unlike many other congenital diseases of the eye, it is not associated with the formation or the eye or early visual development. However, cells of the retina begin to atrophy at an early age in patients. CHM encodes Rab escort protein 1 (REP1), which is sometimes also referred to as component A of Rab geranylgeranyl-transferase. This protein is expressed ubiquitously and is found in all cell types and tissues throughout the body. Through its action on Rab GTPases, REP1 plays a role in the fundamental cellular processes of intracellular vesicle trafficking and recycling. REP1 binds Rabs (member of the Ras subfamily of small GTPases, ~70 members) as they are made by ribosomes on the endoplasmic reticulum. REP1 present newly synthesized, unprenylated Rabs to a catalytic Rab geranylgeranyl-transferase (GGTase) subunit. Rabs undergo prenylation, which involves the covalent attachment of one or more hydrophobic prenyl groups to carboxy-terminal cysteine residues. REP1 also escorts prenylated Rabs to specific destination membranes in the Golgi apparatus (GA) and of diverse cellular vesicles (see Barnard et at (2015) *Cold Spring Harb Prospect Med* 5:a017293). Choroideremia can be prevented or treated by the methods and compositions of the invention. A wild type copy of the CHM gene may be delivered to the eye along with specific nucleases designed to insert the wild type gene via targeted integration either into a safe harbor locus or into the endogenous CHM gene. The nucleases may be delivered either as mRNAs or via an expression vector.

Chronic pain is a major health concern affecting 80 million Americans at some time in their lives with significant associated morbidity and effects on individual quality of life. Chronic pain can result from a variety of inflammatory and nerve damaging events that include cancer, infectious diseases, autoimmune-related syndromes and surgery. Voltage-gated sodium channels (VGSCs) are fundamental in regulating the excitability of neurons and overexpression of these channels can produce abnormal spontaneous firing patterns which underpin chronic pain. There are at least nine different VGSC subtypes in the nervous system, and each subtype can be functionally classified as either tetrodotoxin-sensitive or tetrodotoxin-resistant. Neuronal sodium channel subtypes including Nav1.3, Nav1.7, Nav1.8, and Nav1.9 have been implicated in the processing of nociceptive information. The VGSC Nav1.8 is a tetrodotoxin-resistant sodium channel with a distribution restricted to primary afferent neurons and the majority of Nav1.8-containing afferents transmit nociceptive signals to pain processing areas of the spinal cord. Changes in the expression, trafficking and redistribution of Nav1.8 (encoded by PN3) following inflammation or nerve injury are thought to be a major contributor to the sensitization of afferent nerves and the generation of pain (see Schuelert and McDougall (2012) *Arthritis Res Ther* 14:R5). Rodent models of osteoarthritis have demonstrated that inhibition of Nav1.8 channels on peripheral nerves, with synaptic connections in the spinal cord, is a promising treatment of nociceptive sensory processing and could be helpful to achieve more pronounced and longer lasting analgesia. Thus, the methods and compositions of the invention can be used to treat chronic pain. Specific nucleases can be used to knock out the PN3 gene such that localized expression of the Nav1.8 channel is blocked. The nucleases may be introduced into tissues either as mRNAs encoding the nucleases or as expression vectors.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

DEFINITIONS

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant $(K_d)$ of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Patent Publication No. 20110301073.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 8,586,526; 6,140,081; 6,453,242; 6,746,838; 7,241,573; 6,866,997; 7,241,574 and 6,534,261; see also and WO 03/016496 and U.S. Publication No. 20110301073.

A "selected" zinc finger protein or TALE is a protein not found in nature whose production results primarily from an empirical process such as phage display, interaction trap or hybrid selection. See e.g., U.S. Pat. Nos. 8,586,526; 5,789, 538; 5,925,523; 6,007,988; 6,013,453; 6,200,759; 6,242, 568; 6,733,970; 7,297,491; WO 98/53057; WO 02/099084.

"Recombination" refers to a process of exchange of genetic information between two polynucleotides. For the purposes of this disclosure, "homologous recombination" (HR) refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to re-synthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger or TALEN proteins can be used for additional double-stranded cleavage of additional target sites within the cell. In addition, a CRISPR/Cas system may be similarly employed to induce additional double strand breaks.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the exogenous nucleotide sequence (the "donor sequence" or "transgene") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cells and cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or non-coding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Pat. Nos. 7,914,796; 8,034,598; 8,623,618 and U.S. Patent Publication No. 2011/0201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylates, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins, for example, a fusion between a DNA-binding domain (e.g., ZFP, TALE and/or meganuclease DNA-binding domains) and a functional domain (e.g., endonuclease, meganuclease, ZFP-transcription factor, (ZFP-TF), TALE-transcription factor (TALE-TF), as well as fusion molecules comprising CRIPSR/Cas transcription factor (CRISPR/Cas-TF) or CRISPR/Cas nucleases, etc.) and fusion nucleic acids (for example, a nucleic acid encoding a fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP or TALE. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a DNA-binding domain (ZFP, TALE) is fused to a cleavage domain (e.g., endonuclease domain such as FokI, meganuclease domain, etc.), the DNA-binding domain and the cleavage domain are in operative linkage if, in the fusion polypeptide, the DNA-binding domain portion is able to bind its target site and/or its binding site, while the cleavage (nuclease) domain is able to cleave DNA in the vicinity of the target site. The nuclease domain may also exhibit DNA-binding capability (e.g., a nuclease fused to a ZFP or TALE domain that also can bind to DNA). Similarly, with respect to a fusion polypeptide in which a DNA-binding domain is fused to an activation or repression domain, the DNA-binding domain and the activation or repression domain are in operative linkage if, in the fusion polypeptide, the DNA-binding domain portion is able to bind its target site and/or its binding site, while the activation domain is able to upregulate gene expression or the repression domain is able to downregulate gene expression. In addition, a fusion polypeptide in which a Cas DNA-binding domain is fused to an activation domain, the Cas DNA-binding domain and the activation domain are in operative linkage if, in the fusion polypeptide, the Cas DNA-binding domain portion is able to bind its target site and/or its binding site, while the activation domain is able to up-regulate gene expression. When a fusion polypeptide in which a Cas DNA-binding domain is fused to a cleavage domain, the Cas DNA-binding domain and the cleavage domain are in operative linkage if, in the fusion polypeptide, the Cas DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

The terms "subject" and "patient" are used interchangeably and refer to mammals such as human patients and non-human primates, as well as experimental animals such as rabbits, dogs, cats, rats, mice, rabbits and other animals. Accordingly, the term "subject" or "patient" as used herein means any patient or subject (e.g., mammalian) having a disorder.

Compositions for Altering Gene Expression

Described herein are compositions, for example transcriptional regulators and/or nucleases, which are useful targeting a gene that encodes a protein involved in a NS disorder, for example nucleases that facilitate targeted correction of a mutant gene, targeted inactivation of a gene and/or targeted integration (e.g., of a gene encoding a protein that is aberrantly expressed in the subject with the NS disorder). The compositions can comprise fusion molecules, for example fusion proteins comprising DNA-binding domains fused to functional domains (e.g., transcriptional activation domains, transcriptional repression domains and/or nucleases) and/or nuclease or transcription factor systems including polynucleotide and polypeptide components such as the CRISPR/Cas system.

A. DNA-Binding Domains

Any DNA-binding domain can be used in the nucleases used in the compositions and methods disclosed herein, including but not limited to a zinc finger DNA-binding domain, a TALE DNA binding domain, or a DNA-binding domain from a meganuclease, or a CRIPSR/Cas DNA binding complex.

In certain embodiments, the composition comprises a DNA-binding domain and/or nuclease (cleavage) domain from a meganuclease (homing endonuclease). Naturally-occurring meganucleases recognize 15-40 base-pair cleavage sites and are commonly grouped into four families: the LAGLIDADG family ('LAGLIDADG' disclosed as SEQ ID NO: 28), the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. No. 5,420,032; U.S. Pat. No. 6,833,252; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996) J. Mol. Biol. 263:163-180; Argast et al. (1998) J. Mol. Biol. 280:345-353 and the New England Biolabs catalogue.

In certain embodiments, the homing endonuclease (meganuclease) is engineered (non-naturally occurring). The recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996) J. Mol. Biol. 263:163-180; Argast et al. (1998) J. Mol. Biol. 280:345-353 and the New England Biolabs catalogue. In addition, the DNA-binding specificity of homing endonucleases and meganucleases can be engineered to bind non-natural target sites. See, for example, U.S. Pat. No. 8,021,867; Chevalier et al. (2002) Molec. Cell 10:895-905; Epinat et al. (2003) Nucleic Acids Res. 31:2952-2962; Ashworth et al. (2006) Nature 441:656-659; and Paques et al. (2007) Current Gene Therapy 7:49-66. The DNA-binding domains of the homing endonucleases and meganucleases may be altered in the context of the nuclease as a whole (i.e., such that the nuclease includes the cognate cleavage domain) or may be fused to a heterologous DNA-binding domain (e.g., zinc finger protein or TALE) or to a heterologous cleavage domain. DNA-binding domains derived from meganucleases may also exhibit DNA-binding activity.

In other embodiments, the DNA-binding domain comprises a naturally occurring or engineered (non-naturally occurring) TAL effector DNA binding domain. See, e.g., U.S. Pat. No. 8,586,526, incorporated by reference in its entirety herein. The plant pathogenic bacteria of the genus Xanthomonas are known to cause many diseases in important crop plants. Pathogenicity of Xanthomonas depends on a conserved type III secretion (T3S) system which injects more than 25 different effector proteins into the plant cell. Among these injected proteins are transcription activator-like effectors (TALE) which mimic plant transcriptional activators and manipulate the plant transcriptome (see Kay et at (2007) Science 318:648-651). These proteins contain a DNA binding domain and a transcriptional activation domain. One of the most well characterized TALEs is AvrBs3 from Xanthomonas campestgris pv. Vesicatoria (see Bonas et at (1989) Mol Gen Genet 218: 127-136 and WO2010079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et at (2006) J Plant Physiol 163(3): 256-272). In addition, in the phytopathogenic bacteria Ralstonia solanacearum two genes, designated brg11 and hpx17 have been found that are homologous to the AvrBs3 family of Xanthomonas in the R. solanacearum biovar 1 strain GMI1000 and in the biovar 4 strain RS1000 (See Heuer et at (2007) Appl and Envir Micro 73(13): 4379-4384). These genes are 98.9% identical in nucleotide sequence to each other but differ by a deletion of 1,575 by in the repeat domain of hpx17. However, both gene products have less than 40% sequence identity with AvrBs3 family proteins of Xanthomonas.

Thus, in some embodiments, the DNA binding domain that binds to a target site in a target locus is an engineered domain from a TAL effector similar to those derived from the plant pathogens Xanthomonas (see Boch et al, (2009) Science 326: 1509-1512 and Moscou and Bogdanove, (2009) Science 326: 1501) and Ralstonia (see Heuer et at (2007) Applied and Environmental Microbiology 73(13): 4379-4384); U.S. Pat. Nos. 8,586,526; 8,420,782 and 8,440, 431.

In certain embodiments, the DNA binding domain comprises a zinc finger protein (e.g., a zinc finger protein that binds to a target site in a globin or safe-harbor gene). Preferably, the zinc finger protein is non-naturally occurring in that it is engineered to bind to a target site of choice. See, for example, See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416; U.S. Pat. Nos. 7,888,121; 7,972,854; 6,453, 242; 6,534,261; 6,599,692; 6,503,717; 6,689,558; 7,030, 215; 6,794,136; 7,067,317; 7,262,054; 7,070,934; 7,361, 635; 7,253,273, all incorporated herein by reference in their entireties.

An engineered zinc finger binding or TALE domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 8,586,526; 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in WO 02/077227.

In addition, as disclosed in these and other references, DNA domains (e.g., multi-fingered zinc finger proteins or TALE domains) may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The DNA binding proteins described herein may include any combination of suitable linkers between the individual zinc fingers of the protein. In addition, enhancement of binding specificity for zinc finger binding domains has been described, for example, in WO 02/077227.

Selection of target sites; DNA-binding domains and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496 and U.S. Publication No. 20110301073.

In addition, as disclosed in these and other references, DNA-binding domains (e.g., multi-fingered zinc finger proteins) may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In still further embodiments, the DNA binding domain comprises a DNA-binding single-guide RNA in combination with a CRISPR/Cas nuclease system or a CRISPR/Cas transcription factor. See, e.g., U.S. Pat. No. 8,697,359.

B. Functional Domains

The DNA-binding domains may be operably linked to any functional domain.

In certain embodiments, the functional domain comprises a transcriptional regulatory domain, including an activation domain or a repression domain. Suitable domains for achieving activation include the HSV VP16 activation domain (see, e.g., Hagmann et al., *J. Virol.* 71, 5952-5962 (1997)) nuclear hormone receptors (see, e.g., Torchia et al., *Curr. Opin. Cell. Biol.* 10:373-383 (1998)); the p65 subunit of nuclear factor kappa B (Bitko & Bark *J. Virol.* 72:5610-5618 (1998) and Doyle & Hunt, *Neuroreport* 8:2937-2942 (1997)); Liu et al., *Cancer Gene Ther.* 5:3-28 (1998)), or artificial chimeric functional domains such as VP64 (Beerli et al., (1998) *Proc. Natl. Acad. Sci. USA* 95:14623-33), and degron (Molinari et al., (1999) *EMBO J.* 18, 6439-6447). Additional exemplary activation domains include, Oct 1, Oct-2A, Sp1, AP-2, and CTF1 (Seipel et al., *EMBO J.* 11, 4961-4968 (1992) as well as p300, CBP, PCAF, SRC1 PvALF, AtHD2A and ERF-2. See, for example, Robyr et al. (2000) *Mol. Endocrinol.* 14:329-347; Collingwood et al. (1999) *J. Mol. Endocrinol.* 23:255-275; Leo et al. (2000) *Gene* 245:1-11; Manteuffel-Cymborowska (1999) *Acta Biochim. Pol.* 46:77-89; McKenna et al. (1999) *J. Steroid Biochem. Mol. Biol.* 69:3-12; Malik et al. (2000) *Trends Biochem. Sci.* 25:277-283; and Lemon et al. (1999) *Curr. Opin. Genet. Dev.* 9:499-504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al. (2000) *Gene* 245:21-29; Okanami et al. (1996) *Genes Cells* 1:87-99; Goff et al. (1991) *Genes Dev.* 5:298-309; Cho et al. (1999) *Plant Mol. Biol.* 40:419-429; Ulmason et al. (1999) *Proc. Natl. Acad. Sci. USA* 96:5844-5849; Sprenger-Haussels et al. (2000) *Plant J.* 22:1-8; Gong et al. (1999) *Plant Mol. Biol.* 41:33-44; and Hobo et al. (1999) *Proc. Natl. Acad. Sci. USA* 96:15,348-15,353.

It will be clear to those of skill in the art that, in the formation of a fusion molecule (or a nucleic acid encoding same) between a DNA-binding domain as described herein and a functional domain, either an activation domain or a molecule that interacts with an activation domain is suitable as a functional domain. Essentially any molecule capable of recruiting an activating complex and/or activating activity (such as, for example, histone acetylation) to the target gene is useful as an activating domain of a fusion protein. Insulator domains, localization domains, and chromatin remodeling proteins such as ISWI-containing domains and/or methyl binding domain proteins suitable for use as functional domains in fusion molecules are described, for example, in U.S. Pat. Nos. 6,919,204 and 7,053,264.

Exemplary repression domains include, but are not limited to, KRAB A/B, KOX, TGF-beta-inducible early gene (TIEG), v-erbA, SID, MBD2, MBD3, members of the DNMT family (e.g., DNMT1, DNMT3A, DNMT3B), Rb, and MeCP2. See, for example, Bird et al. (1999) *Cell* 99:451-454; Tyler et al. (1999) *Cell* 99:443-446; Knoepfler et al. (1999) *Cell* 99:447-450; and Robertson et al. (2000) *Nature Genet.* 25:338-342. Additional exemplary repression domains include, but are not limited to, ROM2 and AtHD2A. See, for example, Chem et al. (1996) *Plant Cell* 8:305-321; and Wu et al. (2000) *Plant J.* 22:19-27.

In certain embodiments, the target site bound by the DNA-binding domain is present in an accessible region of cellular chromatin. Accessible regions can be determined as described, for example, in U.S. Pat. No. 6,511,808. If the target site is not present in an accessible region of cellular chromatin, one or more accessible regions can be generated as described in WO 01/83793. In additional embodiments, the DNA-binding domain of a fusion molecule is capable of binding to cellular chromatin regardless of whether its target site is in an accessible region or not. For example, such DNA-binding domains are capable of binding to linker DNA and/or nucleosomal DNA. Examples of this type of "pioneer" DNA binding domain are found in certain steroid receptor and in hepatocyte nuclear factor 3 (HNF3). Cordingley et al. (1987) *Cell* 48:261-270; Pina et al. (1990) *Cell* 60:719-731; and Cirillo et al. (1998) *EMBO J.* 17:244-254.

In other embodiments, the functional (regulatory) domain comprises a nuclease (cleavage) domain. Any suitable cleavage domain can be operatively linked to any DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim et al. (1996) *Proc Nat'l Acad Sci USA* 93(3):1156-1160. See, for example, U.S. Pat. Nos. 7,888,121; 7,972,854; 7,914, 796; 7,951,925; 8,110,379; 8,409,861; 8,586,526; U.S. Patent Publications 20030232410; 20050208489; 20050026157; 20060063231; 20100218264; 20120017290; 20110265198; 20130137104; 20130122591; 20130177983 and 20130177960. Likewise, TALE DNA-binding domains have been fused to nuclease domains to create TALENs. See, e.g., U.S. Pat. No. 8,586,526.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

In certain embodiments, the nuclease is naturally occurring. In other embodiments, the nuclease is non-naturally occurring, i.e., engineered in the DNA-binding domain and/or cleavage domain. For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector nucleases; meganuclease DNA-binding domains with heterologous cleavage domains), or a generic nuclease guided by a specific guide RNA (e.g. a CRPISR/Cas).

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

In some embodiments, a Cas protein may be linked to a heterologous nuclease domain. In some aspects, the Cas protein is a Cas9 protein devoid of nuclease activity linked to a FokI nuclease domain such that double strand cleavage is dependent on dimerization of the FokI nuclease domains.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a DNA binding domain and two Fok I cleavage half-domains can also be used.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in U.S. Publication No. 20070134796, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Pat. Nos. 7,888,121; 8,409,861; and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490

(E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. See, e.g., U.S. Patent Publication No. 20080131962, the disclosure of which is incorporated by reference in its entirety for all purposes.

In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See US Patent Publication No. 20110201055, incorporated by reference herein). Engineered cleavage half-domains described herein can be prepared using any suitable method, for example, by site-directed mutagenesis of wild-type cleavage half-domains (Fok I) as described in U.S. Pat. Nos. 7,888,121; 7,914,796 and 8,034,598.

Alternatively, nucleases may be assembled in vivo at the nucleic acid target site using so-called "split-enzyme" technology (see, e.g., U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

The nuclease domain may also be derived from a homing endonuclease (meganuclease). Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII.

Thus, the nuclease as described herein can comprise any DNA-binding domain and any nuclease.

In certain embodiments, the nuclease comprises a zinc finger DNA-binding domain and a restriction endonuclease nuclease domain, also referred to as a zinc finger nuclease (ZFN).

In other embodiments, the nuclease comprises an engineered TALE DNA-binding domain and a nuclease domain (e.g., endonuclease and/or meganuclease domain), also referred to as TALENs. Methods and compositions for engineering these TALEN proteins for robust, site specific interaction with the target sequence of the user's choosing have been published (see U.S. Pat. No. 8,586,526). In some embodiments, the TALEN comprises an endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel et al., (2013) *Nucl Acid Res:* 1-13, doi: 10.1093/nar/gkt1224). In addition, the nuclease domain may also exhibit DNA-binding functionality.

In still further embodiments, the nuclease comprises a compact TALEN (cTALEN). These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the meganuclease (e.g., TevI) nuclease domain (see Beurdeley et at (2013) *Nat Comm:* 1-8 DOI: 10.1038/ncomms2782). Any TALENs may be used in combination with additional TALENs (e.g., one or more TALENs (cTALENs or FokI-TALENs) with one or more mega-TALs).

Nucleases can be screened for activity prior to use, for example in a yeast-based chromosomal system as described in U.S. Pat. No. 8,563,314. Nuclease expression constructs can be readily designed using methods known in the art. See, e.g., U.S. Pat. Nos. 7,888,121 and 8,409,861; 20030232410; 20050208489; 20050026157; 20060063231; and 20070134796. Expression of the nuclease may be under the control of a constitutive promoter or an inducible promoter, for example the galactokinase promoter which is activated (de-repressed) in the presence of raffinose and/or galactose and repressed in presence of glucose.

In certain embodiments, the nuclease comprises a CRISPR/Cas system. The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR, initially described in *S. pyogenes*, is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences where processing occurs by a double strand-specific RNase III in the presence of the Cas9 protein. Third, the mature crRNA: tracrRNA complex directs Cas9 to the target DNA via Watson-Crick base-pairing between the spacer on the crRNA and the protospacer on the target DNA next to the protospacer adjacent motif (PAM), an additional requirement for target recognition. In addition, the tracrRNA must also be present as it base pairs with the crRNA at its 3' end, and this association triggers Cas9 activity. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cs' proteins are involved with the natural function of the CRISPR/Cas system and serve roles in functions such as insertion of the alien DNA etc.

Type II CRISPR systems have been found in many different bacteria. BLAST searches on publically available genomes by Fonfara et at ((2013) *Nuc Acid Res* 42(4):2377-2590) found Cas9 orthologs in 347 species of bacteria. Additionally, this group demonstrated in vitro CRISPR/Cas cleavage of a DNA target using Cas9 orthologs from *S. pyogenes, S. mutans, S. therophilus, C. jejuni, N. meningitides, P. multocida* and *F. novicida*. Thus, the term "Cas9" refers to an RNA guided DNA nuclease comprising a DNA binding domain and two nuclease domains, where the gene encoding the Cas9 may be derived from any suitable bacteria.

The Cas9 protein has at least two nuclease domains: one nuclease domain is similar to a HNH endonuclease, while the other resembles a Ruv endonuclease domain. The HNH-type domain appears to be responsible for cleaving the DNA strand that is complementary to the crRNA while the Ruv domain cleaves the non-complementary strand. The Cas 9 nuclease can be engineered such that only one of the nuclease domains is functional, creating a Cas nickase (see Jinek et al, ibid). Nickases can be generated by specific mutation of amino acids in the catalytic domain of the enzyme, or by truncation of part or all of the domain such that it is no longer functional. Since Cas 9 comprises two nuclease domains, this approach may be taken on either domain. A double strand break can be achieved in the target DNA by the use of two such Cas 9 nickases. The nickases will each cleave one strand of the DNA and the use of two will create a double strand break.

The requirement of the crRNA-tracrRNA complex can be avoided by use of an engineered "single-guide RNA" (sgRNA) that comprises the hairpin normally formed by the annealing of the crRNA and the tracrRNA (see Jinek et at (2012) *Science* 337:816 and Cong et at (2013) *Sciencexpress*/10.1126/science.1231143). In *S. pyogenes*, the engineered tracrRNA:crRNA fusion, or the sgRNA, guides Cas9 to cleave the target DNA when a double strand RNA:DNA heterodimer forms between the Cas associated RNAs and the target DNA. This system comprising the Cas9 protein and an engineered sgRNA containing a PAM sequence has been used for RNA guided genome editing (see Ramalingam ibid) and has been useful for zebrafish embryo genomic editing in vivo (see Hwang et at (2013) *Nature Biotechnology* 31 (3):227) with editing efficiencies similar to ZFNs and TALENs.

Chimeric or sgRNAs can be engineered to comprise a sequence complementary to any desired target. In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. In certain embodiments, the RNAs comprise 22 bases of complementarity to a target and of the form G[n19], followed by a protospacer-adjacent motif (PAM) of the form NGG. Thus, in one method, sgRNAs can be designed by utilization of a known ZFN target in a gene of interest by (i) aligning the recognition sequence of the ZFN heterodimer with the reference sequence of the relevant genome (human, mouse, or of a particular plant species); (ii) identifying the spacer region between the ZFN half-sites; (iii) identifying the location of the motif G[N20]GG that is closest to the spacer region (when more than one such motif overlaps the spacer, the motif that is centered relative to the spacer is chosen); (iv) using that motif as the core of the sgRNA. This method advantageously relies on proven nuclease targets. Alternatively, sgRNAs can be designed to target any region of interest simply by identifying a suitable target sequence the conforms to the G[n20]GG formula. Along with the complementarity region, an sgRNA may comprise additional nucleotides to extend to tail region of the tracrRNA portion of the sgRNA (see Hsu et at (2013) *Nature Biotech doi:*10.1038/nbt.2647). Tails may be of +67 to +85 nucleotides, or any number therebetween with a preferred length of +85 nucleotides. Truncated sgRNAs may also be used, "tru-gRNAs" (see Fu et al, (2014) *Nature Biotech* 32(3): 279). In tru-gRNAs, the complementarity region is diminished to 17 or 18 nucleotides in length.

Further, alternative PAM sequences may also be utilized, where a PAM sequence can be NAG as an alternative to NGG (Hsu 2014, ibid) using a *S. pyogenes* Cas9. Additional PAM sequences may also include those lacking the initial G (Sander and Joung (2014) *Nature Biotech* 32(4):347). In addition to the *S. pyogenes* encoded Cas9 PAM sequences, other PAM sequences can be used that are specific for Cas9 proteins from other bacterial sources. For example, the PAM sequences shown below (adapted from Sander and Joung, ibid, and Esvelt et al, (2013) *Nat Meth* 10(11):1116) are specific for these Cas9 proteins:

| Species | PAM |
| --- | --- |
| S. pyogenes | NGG |
| S. pyogenes | NAG |
| S. mutans | NGG |
| S. thermophilius | NGGNG |
| S. thermophilius | NNAAAW |
| S. thermophilius | NNAGAA |
| S. thermophilius | NNNGATT |
| C. jejuni | NNNNACA |
| N. meningitides | NNNNGATT |
| P. multocida | GNNNCNNA |
| F. novicida | NG |

Thus, a suitable target sequence for use with a *S. pyogenes* CRISPR/Cas system can be chosen according to the following guideline: [n17, n18, n19, or n20](G/A)G. Alternatively the PAM sequence can follow the guideline G[n17, n18, n19, n20](G/A)G. For Cas9 proteins derived from non-*S. pyogenes* bacteria, the same guidelines may be used where the alternate PAMs are substituted in for the *S. pyogenes* PAM sequences.

Most preferred is to choose a target sequence with the highest likelihood of specificity that avoids potential off target sequences. These undesired off target sequences can be identified by considering the following attributes: i) similarity in the target sequence that is followed by a PAM sequence known to function with the Cas9 protein being utilized; ii) a similar target sequence with fewer than three mismatches from the desired target sequence; iii) a similar target sequence as in ii), where the mismatches are all located in the PAM distal region rather than the PAM proximal region (there is some evidence that nucleotides 1-5 immediately adjacent or proximal to the PAM, sometimes referred to as the 'seed' region (Wu et at (2014) *Nature Biotech doi:*10.1038/nbt2889) are the most critical for recognition, so putative off target sites with mismatches located in the seed region may be the least likely be recognized by the sg RNA); and iv) a similar target sequence where the mismatches are not consecutively spaced or are spaced greater than four nucleotides apart (Hsu 2014, ibid). Thus, by performing an analysis of the number of potential off target sites in a genome for whichever CRIPSR/Cas system is being employed, using these criteria above, a suitable target sequence for the sgRNA may be identified.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. In some aspects, a functional derivative may comprise a single biological property of a naturally occurring Cas protein. In other aspects, a function derivative may comprise a subset of biological properties of a naturally occurring Cas protein. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

Exemplary CRISPR/Cas nuclease systems targeted to specific genes are disclosed for example, in U.S. Publication No. 20150056705.

Thus, the nuclease comprises a DNA-binding domain in that specifically binds to a target site in any gene into which it is desired to insert a donor (transgene) in combination with a nuclease domain that cleaves DNA.

Target Sites

As described in detail above, DNA-binding domains (e.g., ZFPs, TALEs, single-guide RNAs) can be engineered to bind to any sequence of choice in a locus, for example a gene encoding a protein that is involved in a disorder or a safe harbor gene.

In certain embodiments, the DNA-binding domains bind to a sequence in a gene encoding a protein that is involved in a disorder. Non-limiting examples of particular genes involved in disorders that may be targeted (including for alteration of gene expression via transcriptional regulation, correction of mutant genes and/or for targeted inactivation or integration into such genes) include apolipoprotein B (APOB), angiopoietin-like protein 3 (ANGPTL3), proprotein convertase subtilisin/kexin type 9 (PCSK9), apolipoprotein C3 (APOC3), low density lipoprotein receptor (LDLR), C-reactive protein (CRP), apolipoprotein a (Apo (a)), Factor VII, Factor XI, antithrombin III (SERPINC1), phosphatidylinositol glycan class A (PIG-A), C5, alpha-1 antitrypsin (SERPINA1), hepcidin regulation (TMPRSS6), (delta-aminolevulinate synthase 1 (ALAS-1), acylCaA:diacylglycerol acyltransferase (DGAT), miR-122, miR-21, miR-155, miR-34a, prekallikrein (KLKB1), connective tissue growth factor (CCN2), intercellular adhesion molecule 1 (ICAM-1), glucagon receptor (GCGR), glucorticoid receptor (GCCR), protein tyrosine phosphatase (PTP-1B), c-Raf kinase (RAFT), fibroblast growth factor receptor 4 (FGFR4), vascular adhesion molecule-1 (VCAM-1), very late antigen-4 (VLA-4), transthyretin (TTR), survival motor neuron 2 (SMN2), growth hormone receptor (GHR), dystophia myotonic protein kinase (DMPK), cellular nucleic acid-binding protein (CNBP or ZNF9), clusterin (CLU), eukaryotic translation initiation factor 4E (eIF-4e), heat shock protein 27 (HSP 27), signal transduction and activator of transcription 3 protein (STAT3), vascular endothelial growth factor (VEGF), kinesin spindle protein (KIF11), hepatitis B genome, the androgen receptor (AR), Atonal homolog 1 (AtOH1), Vascular endothelial growth factor receptor 1 (FLT1), retinoschisin1 (RS1), retinal pigmented epithelium-specific 65 kDa protein (RPE65), Rab escort protein 1 (CHM), and Sodium channel, voltage gated, type X, alpha subunit (PN3). See, also, Table 1 below, where "KO" refers to knock-out (inactivation) of the gene using one or more nucleases.

TABLE 1

Exemplary targets

| INDICATION | GENE TARGET | GENE ALTERATION |
|---|---|---|
| Familial defective apolipoprotein B (FDB) | APOB | Transcriptional repression or KO |
| Hyperlipidemia | ANGPTL3 | Transcriptional repression or KO |
| Hypercholesterolemia | PCSK9 | KO, transcriptional repression of toxic gain of function mutations. Gene correction to loss of function sequence |
| Familial chylomicronemia syndrome (FCS) | APOC3 | Transcriptional repression or KO |
| Myocardial and cerebral infarction | CRP | Transcriptional activation or KO |
| Myocardial infarction | Apo(A) | Transcriptional repression or KO |
| Thrombotic disease | Factor VII | Transcriptional repression or KO |
| Thrombotic disease | Factor XI | Transcriptional repression or KO |
| Hemophilia | SERPINC1 | Transcriptional repression or KO |
| Paroxysmal nocturnal hemoglobinuria (PNH) | PIG-A | Insertion of a WT transgene |
| Atypical hemolytic-uremic syndrome (aHUS) | C5 | Transcriptional repression or KO |
| Alpha-1 antitrypsin deficiency | SERPINA1 | Transcriptional repression or KO, gene correction |
| Iron overload | TMPRSS6 | Transcriptional repression or KO |
| Acute intermittent porphyria (AIP) | ALAS-1 | Transcriptional repression or KO |
| Non-alcoholic fatty liver disease (NAFLD) | DGAT-2 | Transcriptional repression or KO |
| Hepatitis C (HCV) | miR-122 | Transcriptional repression |
| Hepatitis B (HBV) | HBV genome | Transcriptional repression or KO |
| Hereditary angioedema (HAE) | KLKB1 | Transcriptional repression or KO |
| Cancer, fibrotic disease, ocular disease | CCN2 | Transcriptional repression or KO |

TABLE 1-continued

Exemplary targets

| INDICATION | GENE TARGET | GENE ALTERATION |
|---|---|---|
| Inflammatory disease | ICAM-1 | Transcriptional repression or KO |
| Diabetes | GCCR | Transcriptional repression or KO |
| Diabetes | GCGR | Transcriptional repression or KO |
| Diabetes | PTP-1B | Transcriptional repression or KO |
| Diabetic retinopathy, wet AMD | RAF1 | Transcriptional repression or KO |
| Obesity | FGFR4 | Transcriptional repression or KO |
| Multiple sclerosis (MS) | VCAM-1 | Transcriptional repression or KO |
| Multiple sclerosis (MS) | VLA-4 | Transcriptional repression or KO |
| Cushing's syndrome (CS) | GCCR | Transcriptional repression or KO |
| Transthyretin amyloidosis (TTRA) | TTR | Transcriptional repression or KO, gene correction, insertion of WT transgene |
| Spinal muscular atrophy | SMN-2 | Gene correction |
| Acromegaly | GHR | Transcriptional repression or KO |
| Myotonic dystrophy | DMPK or ZNF9 | Transcriptional repression or KO, gene correction |
| Cancer | CLU | KO |
| Cancer | eIF-4E | Transcriptional repression or KO |
| Cancer | Hsp 27 | Transcriptional repression or KO |
| Cancer | STAT3 | Transcriptional repression or KO |
| Cancer | AR | Transcriptional repression or KO |
| Cancer, Eye Disease | VEGF | Transcriptional repression or KO |
| Cancer | KIF11 | Transcriptional repression or KO |
| Cancer | miR-21 | Transcriptional repression or KO |
| Cancer | miR-155 | Transcriptional repression or KO |
| Cancer, epilepsy | miR-34a | Transcriptional repression or KO |
| Hearing Disorders | AtOH1 | Knock in, up regulation |
| Eye Disease | FLT1 | Knock in, up regulation |
| Eye Disease | RS1 | Knock in, up regulation |
| Eye Disease | RPE65 | Knock in, up regulation |
| Eye Disease | CHM | Knock in, up regulation |
| Chronic Pain | PN3 (SCN10A) | Transcriptional repression or KO |

In other embodiments, the DNA-binding domain binds to a sequence in a safe-harbor gene. Non-limiting examples of safe harbor genes (including for targeted of exogenous molecules such as sequences encoding therapeutic proteins) include, for example, a CCR5 gene, a CXCR4 gene, an HPRT gene, a PPP1R12C (also known as AAVS1) gene, an albumin gene or a Rosa gene. See, e.g., U.S. Pat. Nos. 7,951,925 and 8,110,379; U.S. Publication Nos. 20080159996; 201000218264; 20100291048; 20120017290; 20110265198; 20130137104; 20130122591; 20130177983 and 20130177960 and 20150056705.

Donors

As noted above, insertion of an exogenous sequence (also called a "donor sequence" or "donor" or "transgene"), for example for correction of a mutant gene or for increased expression of a wild-type gene. It will be readily apparent that the donor sequence need not be identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest. Alternatively, a donor molecule may be integrated into a cleaved target locus via non-homologous end joining (NHEJ) mechanisms. See, e.g., U.S. Patent Publication Nos. 20110207221 and 20130326645.

Described herein are methods of targeted insertion of any polynucleotides for insertion into a chosen location. Polynucleotides for insertion can also be referred to as "exogenous" polynucleotides, "donor" polynucleotides or molecules or "transgenes." The donor polynucleotide can be DNA or RNA, single-stranded and/or double-stranded and can be introduced into a cell in linear or circular form. See, e.g., U.S. Patent Publication Nos. 20100047805; 20110281361; and 20110207221. The donor sequence(s) can be contained within a DNA MC, which may be introduced into the cell in circular or linear form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

In certain embodiments, the double-stranded donor includes sequences (e.g., coding sequences, also referred to as transgenes) greater than 1 kb in length, for example between 2 and 200 kb, between 2 and 10 kb (or any value therebetween). The double-stranded donor also includes at least one nuclease target site, for example. In certain embodiments, the donor includes at least 1 target site, for example, for use with a CRISPR/Cas, or 2 target sites, for example for a pair of ZFNs and/or TALENs. Typically, the nuclease target sites are outside the transgene sequences, for example, 5' and/or 3' to the transgene sequences, for cleavage of the transgene. The nuclease cleavage site(s) may be for any nuclease(s). In certain embodiments, the nuclease target site(s) contained in the double-stranded donor are for the same nuclease(s) used to cleave the endogenous target into which the cleaved donor is integrated via homology-independent methods.

The donor is generally inserted so that its expression is driven by the endogenous promoter at the integration site, namely the promoter that drives expression of the endogenous gene into which the donor is inserted. However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. For example, a transgene as described herein may be inserted into a selected locus such that some or none of the endogenous sequences are expressed, for example as a fusion with the transgene. In other embodiments, the transgene is integrated into any endogenous locus, for example a safe-harbor locus. Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

The transgenes carried on the donor sequences described herein may be isolated from plasmids, cells or other sources using standard techniques known in the art such as PCR. Donors for use can include varying types of topology, including circular supercoiled, circular relaxed, linear and the like. Alternatively, they may be chemically synthesized using standard oligonucleotide synthesis techniques. In addition, donors may be methylated or lack methylation. Donors may be in the form of bacterial or yeast artificial chromosomes (BACs or YACs).

The double-stranded donor polynucleotides described herein may include one or more non-natural bases and/or backbones. In particular, insertion of a donor molecule with methylated cytosines may be carried out using the methods described herein to achieve a state of transcriptional quiescence in a region of interest.

The exogenous (donor) polynucleotide may comprise any sequence of interest (exogenous sequence). Exemplary exogenous sequences include, but are not limited to any polypeptide coding sequence (e.g., cDNAs), promoter sequences, enhancer sequences, epitope tags, marker genes, cleavage enzyme recognition sites and various types of expression constructs. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

In a preferred embodiment, the exogenous sequence (transgene) comprises a polynucleotide encoding any polypeptide of which expression in the cell is desired, including, but not limited to any polypeptide involved in a disorder, antibodies, antigens, enzymes, receptors (cell surface or nuclear), hormones, lymphokines, cytokines, reporter polypeptides, growth factors, and functional fragments of any of the above. The coding sequences may be, for example, cDNAs. Non-limiting examples of polypeptides that may be encoded by the exogenous (donor) sequences include growth factors (e.g., growth hormone, insulin-like growth factor-1, platelet-derived growth factor, epidermal growth factor, acidic and basic fibroblast growth factors, transforming growth factor-(3, etc.), to treat growth disorders or wasting syndromes; and antibodies (e.g., human or humanized), to provide passive immunization or protection of a subject against foreign antigens or pathogens (e.g., *H. Pylori*), or to provide treatment of cancer, arthritis or cardiovascular disease; cytokines, interferons (e.g., interferon (INF), INF-a2b and 2a, INF-aN1, INF-(31b, INF-gamma), interleukins (e.g., IL-1 to IL 10), tumor necrosis factor (TNF-a TNF-R), chemokines, granulocyte macrophage colony stimulating factor (GM-CSF), polypeptide hormones, antimicrobial polypeptides (e.g., antibacterial, antifungal, antiviral, and/or antiparasitic polypeptides), enzymes (e.g., adenosine deaminase), gonadotrophins, chemotactins, lipid-binding proteins, filgastim (Neupogen), hemoglobin, erythropoietin, insulinotropin, imiglucerase, sarbramostim, tissue plasminogen activator (WA), urokinase, streptokinase, phenylalanine ammonia lyase, brain-derived neurotrophic factor (BDNF), nerve growth factor (NGF), thrombopoietin (TPO), superoxide dismutase (SOD), adenosine deamidase, catalase calcitonin, endothelian, L-asparaginase pepsin, uricase trypsin, chymotrypsin elastase, carboxypeptidase lactase, sucrase intrinsic factor, calcitonin parathyroid hormone (PTH)-like, hormone, soluble CD4, and antibodies and/or antigen-binding fragments (e.g., FAbs) thereof (e.g., orthoclone OKT-3 (anti-CD3), GP11b/11a monoclonal antibody).

In certain embodiments, the exogenous sequences can comprise a marker gene (described above), allowing selection of cells that have undergone targeted integration, and a linked sequence encoding an additional functionality. Non-limiting examples of marker genes include GFP, drug selection marker(s) and the like.

Additional gene sequences that can be inserted may include, for example, wild-type genes to replace mutated sequences. For example, a wild-type beta globin gene sequence may be inserted into the genome of a stem cell in which the endogenous copy of the gene is mutated. The wild-type copy may be inserted at the endogenous locus, or may alternatively be targeted to a safe harbor locus.

Construction of such expression cassettes, following the teachings of the present specification, utilizes methodologies well known in the art of molecular biology (see, for example, Ausubel or Maniatis). Before use of the expression cassette to generate a transgenic animal, the responsiveness of the expression cassette to the stress-inducer associated with selected control elements can be tested by introducing the expression cassette into a suitable cell line (e.g., primary cells, transformed cells, or immortalized cell lines).

Furthermore, although not required for expression, exogenous sequences may also transcriptional or translational regulatory sequences, for example, promoters, enhancers, insulators, internal ribosome entry sites, sequences encoding 2A peptides and/or polyadenylation signals. Further, the control elements of the genes of interest can be operably linked to reporter genes to create chimeric genes (e.g., reporter expression cassettes).

Targeted insertion of non-coding nucleic acid sequence may also be achieved. Sequences encoding antisense RNAs, RNAi, shRNAs and micro RNAs (miRNAs) may also be used for targeted insertions.

In additional embodiments, the donor nucleic acid may comprise non-coding sequences that are specific target sites for additional nuclease designs. Subsequently, additional nucleases may be expressed in cells such that the original donor molecule is cleaved and modified by insertion of another donor molecule of interest. In this way, reiterative integrations of donor molecules may be generated allowing for trait stacking at a particular locus of interest or at a safe harbor locus.

Delivery

The nucleases, polynucleotides encoding these nucleases, donor polynucleotides and compositions comprising the proteins and/or polynucleotides described herein may be delivered in vivo or ex vivo by any suitable means.

Methods of delivering nucleases as described herein are described, for example, in U.S. Pat. Nos. 8,586,526; 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using vectors containing sequences encoding one or more of compositions described herein. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors. When multiple vectors are used, each vector may comprise a sequence encoding one or multiple nucleases and/or donor constructs.

Conventional viral and non-viral based gene transfer methods can be used to introduce nucleic acids encoding nucleases and donor constructs in cells (e.g., mammalian cells) and target tissues. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389(1994); Remy et al., *Bioconjugate Chem.* 5:647-654(1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et at (2009) *Nature Biotechnology* 27(7):643).

The use of RNA or DNA viral based systems for the delivery of nucleic acids encoding engineered ZFPs take advantage of highly evolved processes for targeting a virus to specific cells in the body and trafficking the viral payload to the nucleus. Viral vectors can be administered directly to subjects (in vivo) or they can be used to treat cells in vitro and the modified cells are administered to subjects (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors is described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Vectors suitable for introduction of polynucleotides described herein also include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Patent Publication No 20090117617.

Recombinant adeno-associated virus vectors (rAAV) may also be used to deliver the compositions described herein. All vectors are derived from a plasmid that retains only the AAV inverted terminal repeats flanking the transgene expression cassette. Efficient gene transfer and stable transgene delivery are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6, AAV8, AAV9 and AAVrh10, pseudotyped AAV such as AAV2/8, AAV2/5 and AAV2/6 and all variants thereof, can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual subject, typically by systemic administration (e.g., intravenous, intraperitoneal, intramuscular, intrathecal, intratracheal, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

In certain embodiments, the compositions (including fusion proteins, CRISPR/Cas systems and/or modified cells) as described herein (e.g., polynucleotides and/or proteins) are delivered directly in vivo. The compositions (cells, polynucleotides and/or proteins) may be administered directly into the CNS, including but not limited to direct injection into the brain or spinal cord. One or more areas of the brain may be targeted, including but not limited to, the hippocampus, the substantia nigra, the nucleus basalis of Meynert (NBM), the striatum and/or the cortex. Alternatively or in addition to CNS delivery, the compositions may be administered systemically (e.g., intravenous, intraperitoneal, intracardial, intramuscular, intrathecal, subdermal, and/or intracranial infusion). Methods and compositions for delivery of compositions as described herein directly to a subject (including directly into the CNS) include but are not limited to direct injection (e.g., stereotactic injection) via needle assemblies. Such methods are described, for example, in U.S. Pat. Nos. 7,837,668; 8,092,429, relating to a needle assembly for delivery of compositions to the brain and U.S. Patent Publication No. 20060239966 as well as U.S. Pat. Nos. 6,180,613 and 6,503,888 (AAV-mediated delivery of DNA to cells of the nervous system) and U.S. Pat. Nos. 6,998,118 and 7,101,540 (gene delivery to neuronal cells), incorporated herein by reference in their entireties.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., Remington's Pharmaceutical Sciences, 17th ed., 1989).

It will be apparent that the nuclease-encoding sequences and donor constructs can be delivered using the same or different systems. For example, a donor polynucleotide can be carried by a plasmid, while the one or more nucleases can be carried by a AAV vector. Furthermore, the different vectors can be administered by the same or different routes (intramuscular injection, tail vein injection, other intravenous injection, intraperitoneal administration and/or intramuscular injection. The vectors can be delivered simultaneously or in any sequential order.

Thus, the instant disclosure includes in vivo or ex vivo treatment of diseases and conditions that are amenable to insertion of a transgenes encoding a therapeutic protein, for example treatment of disorders via nuclease-mediated integration of a gene encoding a protein aberrantly expressed in a subject with the disorder.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFP nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

Suitable cells include but not limited to eukaryotic and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells, any plant cell (differentiated or undifferentiated) as well as insect cells such as *Spodopterafugiperda* (Sf), or fungal cells such as *Saccharomyces, Pichia* and *Schizosaccharomyces*. In certain embodiments, the cell line is a CHO-K1, MDCK or HEK293 cell line. Additionally, primary cells may be isolated and used ex vivo for reintroduction into the subject to be treated following treatment with the nucleases (e.g. ZFNs or TALENs) or nuclease systems (e.g. CRISPR/Cas). Suitable primary cells include neuronal cells, peripheral blood mononuclear cells (PBMC), and other blood cell subsets such as, but not limited to, CD4+ T cells or CD8+ T cells. Suitable cells also include stem cells such as, by way of example, embryonic stem cells, induced pluripotent stem cells, hematopoietic stem cells (CD34+), neuronal stem cells and mesenchymal stem cells.

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow.

Stem cells that have been modified may also be used in some embodiments. For example, stem cells that have been made resistant to apoptosis may be used as therapeutic compositions where the stem cells also contain the ZFPs, TALEs, ZFNs, TALENs, CRISPR/Cas systems and/or donors of the invention. Resistance to apoptosis may come about, for example, by knocking out BAX and/or BAK using BAX- or BAK-specific nucleases (see, U.S. Pat. No. 8,597,912) in the stem cells, or those that are disrupted in a caspase, again using caspase-6 specific ZFNs for example. Alternatively, resistance to apoptosis can also be achieved by the use of caspase inhibitors like Z-VAD-FMK (carbobenzoxy-valyl-alanyl-aspartyl-[O-methyl]-fluoromethyl-ketone).

Vectors (e.g., retroviruses, adenoviruses, liposomes, etc.) containing therapeutic ZFPs, TALEs, ZFNs, TALENs, CRISPR/Cas system and/or donor nucleic acids can also be administered directly to an organism for transduction of cells in vivo. Alternatively, naked DNA or mRNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

The effective amount of nuclease(s) and donor to be administered will vary from patient to patient and according to the therapeutic polypeptide of interest. Accordingly, effective amounts are best determined by the physician administering the compositions and appropriate dosages can be determined readily by one of ordinary skill in the art. After allowing sufficient time for integration and expression (typically 4-15 days, for example), analysis of the serum or other tissue levels of the therapeutic polypeptide and comparison to the initial level prior to administration will determine whether the amount being administered is too low, within the right range or too high. Suitable regimes for initial and subsequent administrations are also variable, but are typified by an initial administration followed by subsequent administrations if necessary. Subsequent administrations may be administered at variable intervals, ranging from daily to annually to every several years. One of skill in the art will appreciate that appropriate immunosuppressive techniques may be recommended to avoid inhibition or blockage of transduction by immunosuppression of the delivery vectors, see e.g., Vilquin et al., (1995) *Human Gene Ther.* 6:1391-1401.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Applications

The methods and compositions disclosed herein are for modifying expression of protein, or correcting an aberrant gene sequence that encodes a gene product expressed in a disorder. Thus, the methods and compositions provide for the treatment and/or prevention of such disorders. Genome editing, for example of stem cells, is used to correct an aberrant gene, insert a wild type gene, or change the expression of an endogenous gene. By way of non-limiting example, a wild type gene may be inserted into a cell to provide the proteins deficient and/or lacking in the subject and thereby treat a disorder caused by faulty gene product expression. Alternatively or in addition, genomic editing with or without administration of the appropriate donor, can correct the faulty endogenous gene, e.g., correcting the point mutation in gene encoding a gene product involved in a disorder, to restore expression of the gene and/or treat a the disorder.

The following Examples relate to exemplary embodiments of the present disclosure in which the nuclease comprises a zinc finger nuclease (ZFN) or TALEN. It will be appreciated that this is for purposes of exemplification only and that other nucleases can be used, for instance additional TALENs (e.g., Mega-TALs and/or compact TALENs), homing endonucleases (meganucleases) with engineered DNA-binding domains and/or fusions of naturally occurring or engineered homing endonucleases (meganucleases) and DNA-binding domains and heterologous cleavage domains and/or a CRISPR/Cas system comprising an engineered single guide RNA. It will also be appreciated that these examples serve as exemplification for use of an engineered transcription factor (e.g. ZFP-TF, TALE-TF, CRISPR/Cas-TF) as well.

EXAMPLES

Example 1

Design, Construction and General Characterization of Compositions that Alter Disease-Related Genes Zinc finger proteins and TALEs that bind to disease-related genes operably linked to transcriptional regulatory or nuclease domains are designed and incorporated into plasmids, AAV or adenoviral vectors or made into mRNA essentially as described in Urnov et al. (2005) *Nature* 435(7042):646-651, Perez et at (2008) *Nature Biotechnology* 26(7):808-816, and as described in U.S. Pat. Nos. 8,586,526 and 6,534,261.

sgRNAs for use in the CRISPR/Cas system are made synthetically by methods known in the art (see Hsu et al, ibid or Sternberg et al, (2014) *Nature* 507: 62)). The sgRNAs are engineered as described above and are designed to target a sequence in a gene on interest. Table II below shows the genomic coordinates of the genes of the invention. These coordinates are derived from the UCSC Genome Browser, hg19 assembly. Thus, sgRNAs, ZFPs or TALEs are designed to target regions within the bounds of the genes.

TABLE II

Genomic coordinates of exemplary genes

| GENE TARGET | Position | Representative Accession (cDNA) RefSeq |
|---|---|---|
| APOB | chr2: 21224301-21266945 | (NM_000384) |
| ANGPTL3 | Chr1: 62454726..62688368 | (NG_028169) |
| PCSK9 | chr1: 55505149-55530526 | (NM_174936) |
| APOC3 | chr11: 116700624-116703787 | (NM_000040.1) |
| CRP | chr1: 159682079-159684379 | (NM_000567) |
| Apo(A) | chr11: 116706469-116708338 | (NM_000039) |
| Factor VII | chr13: 113760102-113774995 | (NM_000131) |
| Factor XI | chr4: 187187118-187196051 | (NM_000128) |
| SERPINC1 | chr1: 173,872,942-173,886,516 | (NM_000488) |
| PIG-A | chrX: 15337573-15343274 | (NM_020473) |
| C5 | chr9: 123714614-123812554 | (NM_001735) |
| SERPINA1 | chr14: 94843084-94849578 | (NM_001002235) |
| TMPRSS6 | chr22: 37461479-37499693 | (NM_153609) |
| ALAS-1 | chr3: 52232099-52248343 | (NM_199166) |
| DGAT-2 | chr11: 75479778-75512581 | (NM_032564) |
| miR-122 | chr18: 56118306-56118390 | (MI0000442) |
| HBV genome | N/A | (X51970) |
| KLKB1 | chr4: 187148672-187179625 | (NM_000892) |
| CCN2 (CTGF) | chr6: 132269317-132272518 | (NM_001901) |
| ICAM-1 | chr19: 10381517-10397291 | (NM_000201) |
| GCGR | chr17: 79762008-79771889 | (NM_000160) |
| PTP-1B (PTPN1) | chr20: 49126858-49201300 | (NM_002827.3) |
| RAF1 | chr3: 12625100-12650834 | (NM_002880) |
| FGFR4 | chr5: 176516551-176518105 | (NM_022963) |
| VCAM-1 | chr1: 101185196-101204601 | (NM_001078.3) |
| VLA-4-CD49d | chr2: 182321619-182351128 | (NM_000885) |
| VLA-4-CD29 (ITBGB1) | chr10: 33189246-33247293 | (NM_002211.3) |
| GCCR (NR3C1) | chr5: 142657496-142783254 | (NM_001024094) |
| TTR | chr18: 29171730-29178986 | (NM_001087879) |
| SMN-2 | chr5: 70220768-70248842 | (NM_022875) |
| GHR | chr5: 42423877-42721980 | (NM_000163) |
| DMPK (ZNF9) | chr19: 46272967-46285815 | (NM_001081563) |
| CLU | chr8: 27454434-27468954 | (NR_038335) |
| eIF-4E | chr4: 99799607-99851786 | (NM_001968) |
| Hsp 27 (HSBP1) | chr7: 75931875-75933614 | (NM_001540) |
| STAT3 | chr17: 40468845-40500534 | (NM_213662) |
| AR | chrX: 66763874-66909600 | (NM_000044) |
| VEGF | chr6: 43737946-43754223 | (NM_001204384) |
| KIF11 | chr10: 94352825-94415152 | (NM_004523) |
| miR-21 | chr17: 57918627-57918698) | (NR_029493) |
| miR-155 | chr21: 26946292-26946356 | (NR_030784.1) |
| miR-34a | chr1: 9211727-9211836 | (NR_029610) |
| SOC3 | chr17: 76352858-76356160 | (NM_003955) |
| AtOH1 | chr4: 94,750,078-94,751,142 | (NM_005172.1) |
| FLT1 | chr13: 28,874,483-29,069,265 | (NM_002019.4) |
| RS1 | chrX: 18,657,808-18,690,223 | (NM_000330.3) |
| RPE65 | chr1: 68,894,507-68,915,642 | (NM_000329.2) |
| CHM | chrX: 85,116,185-85,302,566 | (NM_000390) |
| PN3 (SCN10A) | chr3: 38,738,837-38,835,501 | (NM_006514.3) |

Example 2

Nuclease Activity

ZFNs and TALENs targeting the selected locus are made as described above. The Cel-I assay (Surveyor™, Transgenomics) as described in Perez et al. (2008) *Nat. Biotechnol.* 26: 808-816 and Guschin et al. (2010) *Methods Mol Biol.* 649:247-56), is used to detect nuclease-induced modifications of the target gene in K562 cells orHCT116 cells.

Figure 1B:
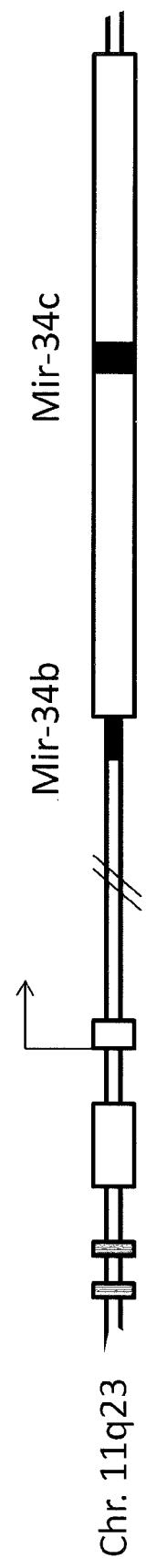
Figure 2:
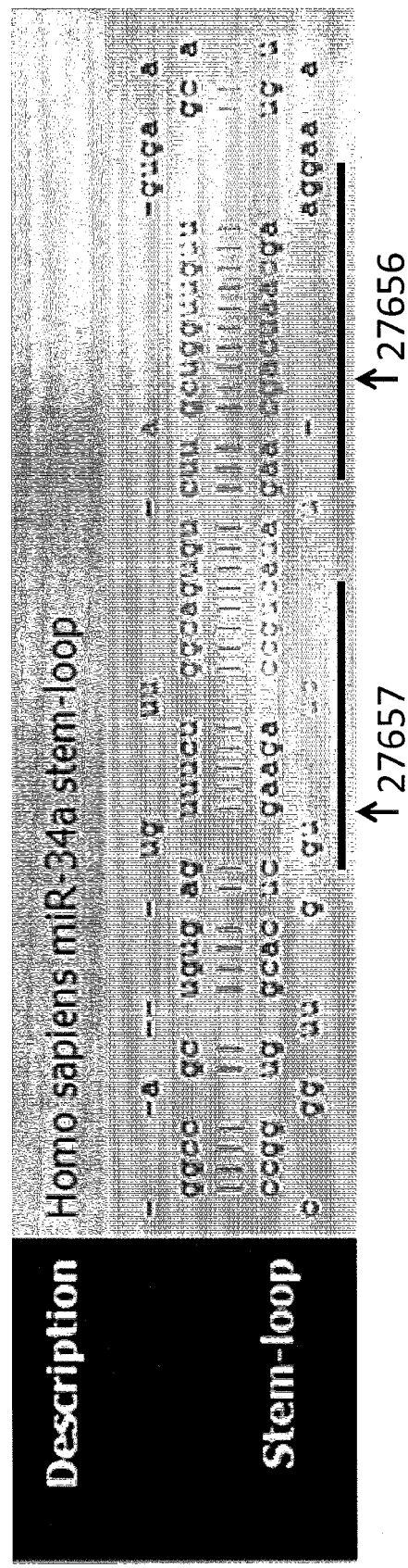
FIG. 2 depicts a miR-34a stem loop secondary structure (SEQ ID NO:1), indicating where the ZFN pair 27657/27656 binds the DNA sequence corresponding to this RNA.
Figure 3:
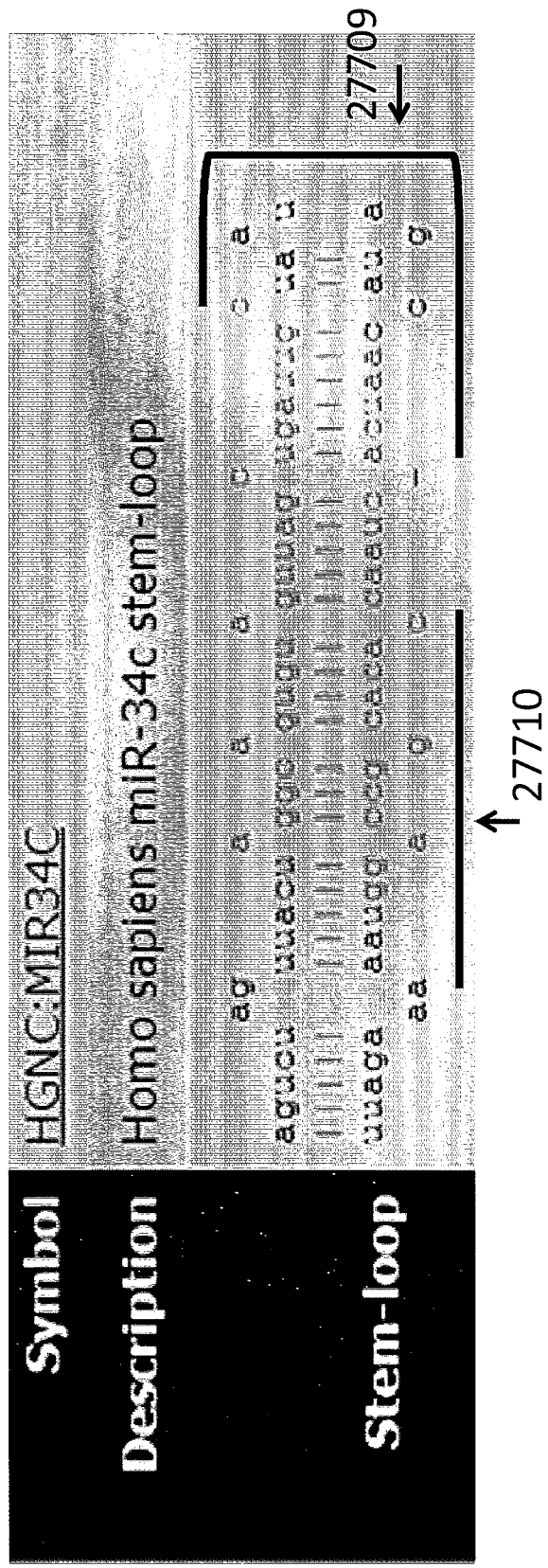
FIG. 3 depicts a miR-34c stem loop secondary structure (SEQ ID NO:2), indicating where the ZFN pair 27710/27709 binds the DNA sequence corresponding to this RNA.
Figure 4B:
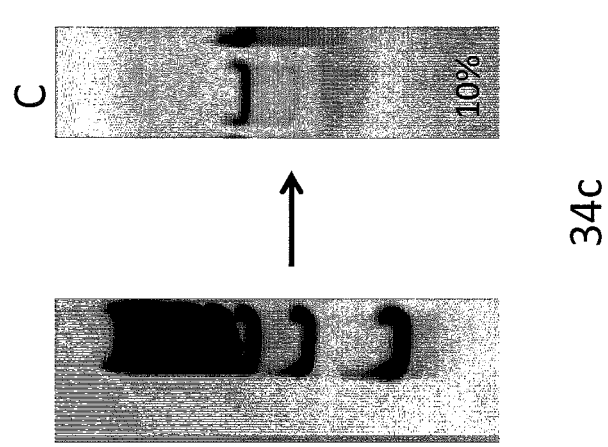
FIGS. 4A and 4B depict gels showing the activity of the ZFN pairs.
Figure 4A:
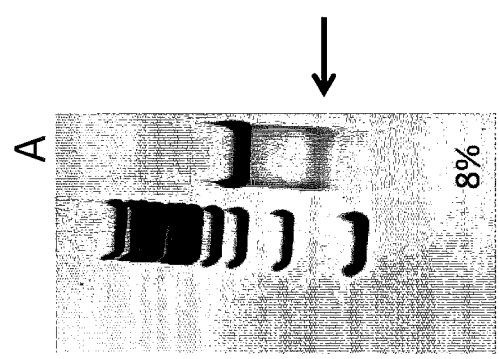

In this assay, PCR-amplification of the target site is followed by quantification of insertions and/or deletions ("indels") using the mismatch detecting enzyme Cel-I (Yang et al. (2000) *Biochemistry* 39: 3533-3541) which provided a lower-limit estimate of DSB frequency. ZFNs against the miR-loci were made to knock out these genes. MiR-34a is on a separate location that miR-34b and 34c (see FIG. 1). Two sets of ZFNs were tested to target the stem loops in the miR 34a and miR 34c loci (see FIGS. 2 and 3), and these ZFNs are shown below in Table III. The first column in this table is an internal reference name (number) for a ZFP and the target sequence. "F" refers to the finger and the number following "F" refers to which zinc finger (e.g., "F1" refers to finger 1). Nucleotides in the target site that are contacted by the ZFP recognition helices are indicated in uppercase letters; non-contacted nucleotides indicated in lowercase. The nucleases were made and tested as described above and found to be active (see FIG. 4).

TABLE III

MiR 34-specific ZFPs

| SBS #/ (Target) | miRF1 | F2 | F3 | F4 | F5 |
|---|---|---|---|---|---|
| 27657 (taCTGCC CtAGAAGT GCTgcacgt tgtg) SEQ ID NO: 3 | 34AQSSDLSR (SEQ ID NO: 7) | WKWNLRA (SEQ ID NO: 8) | QNAHRK T_(SEQ ID NO: 9) | DRSDLSR (SEQ ID NO: 10) | RRST LRS (SEQ ID NO: 11) |
| 27656 (acTTGCT GATTGCTT CCttactat tgct) SEQ ID NO: 4 | 34ADSSDRKK (SEQ ID NO: 12) | QSSDLSR (SEQ ID NO: 7) | YKWTLR N (SEQ ID NO: 13) | RSDVLSE (SEQ ID NO: 14) | RNFS LTM (SEQ ID NO: 15) |
| 27709 (gtGATTG GTACTATT AGcaatca gctaa) SEQ ID NO: 5 | 34CRSDNLST (SEQ ID NO: 16) | WRDSLLA (SEQ ID NO: 17) | DRSNRIK (SEQ ID NO: 18) | RSDHLST (SEQ ID NO: 19) | TSAN LSR (SEQ ID NO: 20) |
| 27710 (acCACAC GGCCAGGT AAaaagatt tggg) SEQ ID NO: 6 | 34CQSANRTK (SEQ ID NO: 21) | RSAHLSR (SEQ ID NO: 22) | DRSDLSR (SEQ ID NO: 10) | RSDTLST (SEQ ID NO: 23) | DSSN RIN (SEQ ID NO: 24) |

Example 3

In Vivo Cleavage of a Genetic Locus in Mice

The mouse locus specific ZFNs which target a sequence a genetic locus of interest are tested in vivo. The ZFNs are introduced into an AAV2/8 vector as described previously (Li et at (2011) *Nature* 475 (7355): 217). To facilitate production in the baculovirus system, the vector AAV2/8.2 is used for preparations destined for baculoviral production. AAV2/8.2 differs from the AAV2/8 vector in that a portion of the AAV8 capsid has been removed and replaced by a same region from the AAV2 capsid creating a chimeric capsid. The region is the phospholipase A2 domain in VP1. Production of the ZFN containing virus particles is done either by preparation using a HEK293 system or a baculovirus system using standard methods in the art (See Li et al, ibid, see e.g. U.S. Pat. No. 6,723,551).

The virus particles are then administered to normal male mice (n=6) using a single dose of 200 microliter of 1.0e11 total vector genomes of either AAV2/8 or AAV2/8.2 encoding the mouse locus-specific ZFN. 14 days post administration of rAAV vectors, mice are sacrificed, livers harvested and processed for DNA or total proteins using standard methods known in the art. Detection of AAV vector genome copies is performed by quantitative PCR. Briefly, qPCR primers were made specific to the bGHpA sequences within the AAV as follows:

```
Oligo200 (Forward)
                                  (SEQ ID NO: 25)
5'-GTTGCCAGCCATCTGTTGTTT-3'

Oligo201 (Reverse)
                                  (SEQ ID NO: 26)
5'-GACAGTGGGAGTGGCACCTT-3'

Oligo202 (Probe)
                                  (SEQ ID NO: 27)
5'-CTCCCCCGTGCCTTCCTTGACC-3'
```

Cleavage activity of the ZFN is measured using a Cel-1 assay performed using a LC-GX apparatus (Perkin Elmer), according to manufacturer's protocol. Expression of the ZFNs in vivo is measured using a FLAG-Tag system according to standard methods. The results demonstrate that the ZFNs are expressed, and that they are active in cleaving the target in the mouse liver gene. Mismatch repair following ZFN cleavage (indicated % indels) is detected.

Locus-specific TALENs are also tested as set forth in U.S. Publication Nos. 20130177983 and 20130177960 (and incorporated by reference in their entireties).

Example 4

In Vivo Insertion of a Corrected Disease Associated Gene in Mice

The murine locus specific ZFNs or TALENs are then used to introduce transgene encoding a therapeutic gene product into a safe harbor locus for expression. In the donor constructs, the therapeutic gene is flanked by sequences homologous to the safe harbor gene. 5' of the transgene, the donor constructs all contain sequences homologous to the murine safe harbor gene, while 3' of the gene, the constructs contain sequences homologous to the murine safe harbor gene.

The donor constructs are then incorporated into an AAV genome and the resulting AAV particles containing the donors are then purified using methods know in the art. The material is used to produce AAV viruses containing AAV-donor genomes using the triple transfection method into HEK 293T cells and purified on CsCl density gradients as has been described (see Ayuso et al. (2010) *Gene Ther* 17(4), 503-510). AAV vector will be diluted in PBS prior to injection. A range of 5e9 to 5e13 v.g. AAV-donor vector particles will be used in conjunction with 1e9 to 1e12 vg of AAV-ZFN vector particles via tail vein or intraperitoneal injections of the viruses in wild-type, or disease model mice. AAV-ZFN genomes, described previously, containing the mouse safe harbor-specific ZFNs will be used, in combination with the AAV-donors. Cel-I and PCR assays will be performed on liver DNA isolated at various time points to determine the frequency of NHEJ- and ZFN-induced donor insertion. Southern blots may also be used. As per standard protocol, quantification of transgene products in plasma will be performed using an ELISA kit or using a FLAG Tag ELISA kit. Standard Western blots are also performed. The results demonstrate that these corrective transgenes can increase the expression of the therapeutic protein in vivo.

Example 5

Activity of Engineered Nucleases In Vivo: Rhesus Macque

Locus specific ZFNs are tested in vivo in Rhesus monkeys as follows:

In brief, Rhesus monkeys (purpose-bred), ages 2 to 4 years old with weights of 3 to 4.6 kg are prescreened for the presence of rAAV 2/6 and 2/8 neutralizing antibodies, the genotype of the locus of interest, and normal serum chemistry and hematology. The animals are socially housed (up to 3 animals of same dosing group housed together). Vector administration is performed by IV infusion into a peripheral vein at a rate of 1 mL/min, for a dosing duration ranging from ~10-30 minutes. The monkeys are evaluated throughout the study for mortality/moribundity, routine clinical observations, cage side observations and food consumption (daily), body weights (prestudy and weekly), clinical pathology including liver enzyme levels (ALT and AST), clinical chemistry and hematology, and coagulation using routine methodologies. Liver biopsies are performed and tissues were examined for histopathology and the pharmacokinetics of rAAV vectors as well as evaluated for gene modification by miSEQ (Illumina) and ZFN expression by Western analysis. Anti-drug antibody analysis was done throughout the study and PBMCs are isolated from whole blood for EliSpot analysis according to standard protocols. Gross and microscopic pathology are performed on tissues evaluation at the end of the study.

Enzyme-linked immunosorbent spot assays (ELISPOT, see Markusic et at (2013), *EMBO Mol Med* 5:1698-1709) are performed on the spleen and mesenteric lymph node tissue isolated from the animals at day 65 and no immune response is elicited against the AAV8 capsid or the ZFN transgenes in the animals.

In a separate study, three groups of two animals each are evaluated for ZFN-mediated insertion of an transgene into the safe harbor locus of rhesus macaques. The ZFNs are used as described and comprise either wild type FokI nuclease cleavage domains (labeled "Fok1 WT") or engineered domains (labeled "Fok1 eHiFi", see U.S. Publication No. 20110201055), in either an AAV2/8 or AAV2/6 vector. Animals that receive the donor containing AAVs are given the donor (with safe harbor homology arms) in an AAV2/8 vector.

Animals receiving ZFNs only (no donor) show robust cleavage at day 14 post-administration. Western analysis is performed on the samples to evaluate ZFN expression. In addition, expression of transgene donor encoded protein is detected in the plasma in animals that had received both the ZFNs and donor vectors.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A fusion molecule comprising (i) an engineered nuclease that binds to a target site within SEQ NOs:3, 4, 5 or 6 of an endogenous gene that produces a microRNA (miRNA), and (ii) a cleavage domain.

2. A polynucleotide encoding one or more fusion molecules of claim 1.

3. An isolated cell comprising one or more fusion molecules according to claim 1.

4. The cell of claim 3, wherein the cell is a stem cell.

5. The cell of claim 3, wherein the stem cell is selected from the group consisting of an embryonic stem cell (ESC), an induced pluripotent stem cell (iPSC), a hepatic stem cell and a liver stem cell.

6. The fusion molecule of claim 1, wherein the engineered nuclease is a zinc finger nuclease.

7. The zinc finger nuclease of claim 6 wherein the endogenous gene is MiR-34 and the zinc finger protein comprises 5 zinc, finger domains, each domain comprising a recognition helix region, wherein the zinc finger protein comprises the recognition helix regions as shown in a single row of Table III.

8. A kit comprising a fusion molecule according to claim 1.

9. A kit comprising a polynucleotide according to claim 2.

10. A method of cleaving an endogenous gene that produces an miRNA in a cell, the method comprising:
    introducing, into the cell, one or more expression vectors comprising at least one polynucleotide according to claim 2, under conditions such that the one or more fusion molecules are expressed and the miRNA-producing gene is cleaved.

11. The method of claim 10, wherein the polynucleotide comprises an AAV vector.

12. The method of claim 10, wherein the polynucleotide is an mRNA.

* * * * *

SEQUENCE LISTING

```
<160> NUMBER OF SEQ ID NOS: 28

<210> SEQ ID NO 1
<211> LENGTH: 110
<212> TYPE: RNA
<213> ORGANISM: Homo sapiens

<400> SEQUENCE: 1
ggccagcugu gaguguuucu uuggcagugu cuuagcuggu uguugugagc aauaguaagg      60
aagcaaucag caaguauacu gcccuagaag ugcugcacgu uguggggccc                110

<210> SEQ ID NO 2
<211> LENGTH: 77
<212> TYPE: RNA
<213> ORGANISM: Homo sapiens

<400> SEQUENCE: 2
agucuaguua cuaggcagug uaguuagcug auugcuaaua guaccaauca cuaaccacac      60
ggccagguaa aaagauu                                                    77

<210> SEQ ID NO 3
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 3
tactgcccta gaagtgctgc acgttgtg                                          28

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
acttgctgat tgcttcctta ctattgct                                          28

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gtgattggta ctattagcaa tcagctaa                                          28

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
accacacggc caggtaaaaa gatttggg                                          28

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Ser Ser Asp Leu Ser Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Lys Trp Asn Leu Arg Ala
1               5
```

-continued

```
<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Asn Ala His Arg Lys Thr
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Arg Ser Asp Leu Ser Arg
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Arg Ser Thr Leu Arg Ser
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Ser Ser Asp Arg Lys Lys
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Lys Trp Thr Leu Arg Asn
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 14

Arg Ser Asp Val Leu Ser Glu
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Asn Phe Ser Leu Thr Met
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ser Asp Asn Leu Ser Thr
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Trp Arg Asp Ser Leu Leu Ala
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Arg Ser Asn Arg Ile Lys
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Ser Asp His Leu Ser Thr
1               5
```

```
<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Ser Ala Asn Leu Ser Arg
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Ser Ala Asn Arg Thr Lys
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ser Ala His Leu Ser Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Ser Asp Thr Leu Ser Thr
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Ser Ser Asn Arg Ile Asn
1               5

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 25
gttgccagcc atctgttgtt t                                              21

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gacagtggga gtggcacctt                                                20

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ctcccccgtg ccttccttga cc                                             22

<210> SEQ ID NO 28
<211> LENGTH: 9
<212> TYPE: PRT
<213> ORGANISM: Unknown
<220> FEATURE:
<223> OTHER INFORMATION: Description of Unknown: 'LAGLIDADG' family
      motif peptide

<400> SEQUENCE: 28

Leu Ala Gly Leu Ile Asp Ala Asp Gly
1               5
```